US011078495B2

(12) United States Patent
Kafri

(10) Patent No.: US 11,078,495 B2
(45) Date of Patent: Aug. 3, 2021

(54) METHODS AND COMPOSITIONS FOR INTEGRATION DEFECTIVE LENTIVIRAL VECTORS

(71) Applicant: The University of North Carolina at Chapel Hill, Chapel Hill, NC (US)

(72) Inventor: Tal Kafri, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 173 days.

(21) Appl. No.: 15/768,438

(22) PCT Filed: Oct. 14, 2016

(86) PCT No.: PCT/US2016/057041
§ 371 (c)(1),
(2) Date: Apr. 13, 2018

(87) PCT Pub. No.: WO2017/066570
PCT Pub. Date: Apr. 20, 2017

(65) Prior Publication Data
US 2018/0320198 A1 Nov. 8, 2018

Related U.S. Application Data

(60) Provisional application No. 62/241,986, filed on Oct. 15, 2015.

(51) Int. Cl.
*C12N 15/86* (2006.01)
*C12N 15/113* (2010.01)

(52) U.S. Cl.
CPC ............ *C12N 15/86* (2013.01); *C12N 15/113* (2013.01); *C12N 2310/122* (2013.01); *C12N 2310/14* (2013.01); *C12N 2310/531* (2013.01); *C12N 2330/51* (2013.01); *C12N 2710/22022* (2013.01); *C12N 2740/16043* (2013.01); *C12N 2830/30* (2013.01)

(58) Field of Classification Search
None
See application file for complete search history.

(56) References Cited

U.S. PATENT DOCUMENTS

| | | | | |
|---|---|---|---|---|
| 8,530,153 B1 * | 9/2013 | Kung | .................... | C12N 5/0639 435/325 |
| 9,284,552 B2 * | 3/2016 | Spayd | .................... | C12N 15/86 |
| 2010/0323403 A1 | 12/2010 | Kafri | | |
| 2013/0345115 A1 * | 12/2013 | An | ........................ | C07K 14/00 514/1.2 |

FOREIGN PATENT DOCUMENTS

| | | | |
|---|---|---|---|
| WO | WO 2010/105251 A2 | 9/2010 | |
| WO | WO 2011/025566 A1 | 3/2011 | |
| WO | WO-2013149167 A1 * | 10/2013 | ..... A61K 39/001151 |

OTHER PUBLICATIONS

Sadaie et al., Iranian Biomedical Journal, Oct. 1998, 2(3 & 4):95-103. (Year: 1998).*
International Search Report and the Written Opinion of the International Searching Authority corresponding to International Patent Application No. PCT/US2016/057041 (9 pages) (dated Jan. 19, 2017).
Manjunath et al. "Lentiviral delivery of short hairpin RNAs" *Advanced Drug Delivery Reviews* 61(9):732-745 (2009).
International Preliminary Report on Patentability corresponding to International Patent Application No. PCT/US2016/057041 (7 pages) (dated Apr. 17, 2018).
Batz et al. "Chemical Vapor Deposition of Aminopropyl Silanes in Microfluidic Channels for Highly Efficient Microchip Capillary Electrophoresis-Electrospray Ionization-Mass Spectrometry" *Analytical Chemistry* 86:3493-3500 (2014).
Chambers et al. "Monolithic Integration of Two-Dimensional Liquid Chromatography-Capillary Electrophoresis and Electrospray Ionization on a Microfluidic Device" *Analytical Chemistry* 83:842-849 (2011).
Mellors et al. "Integrated Microfluidic Device for Automated Single Cell Analysis Using Electrophoretic Separation and Electrospray Ionization Mass Spectrometry" *Analytical Chemistry* 82:967-973 (2010).
Mellors et al. "Hybrid Capillary/Microfluidic System for Comprehensive Online Liquid Chromatography-Capillary Electrophoresis-Electrospray Ionization-Mass Spectrometry" *Analytical Chemistry* 85:4100-4106 (2013).
Nightingale et al. "Transient Gene Expression by Nonintegrating Lentiviral Vectors" *Molecular Therapy* 13(6):1121-1132 (2006).
Ramsey et al. "Generating Electrospray from Microchip Devices Using Electroosmotic Pumping" *Analytical Chemistry* 69:1174-1178 (1997).

(Continued)

Primary Examiner — Nicole Kinsey White
(74) Attorney, Agent, or Firm — Myers Bigel, P.A.

(57) ABSTRACT

The present invention provides an integration-defective lentiviral vector based on a parental lentivirus and related methods, the integration-defective lentiviral vector including one or more of the following: (a) a mutation, deletion or other modification of one or more binding sites for a host factor involved in gene silencing; (b) an addition of one or more binding sites for a transcription activator, which can be natural (such as but not limited to ubiquitous and/or tissue/cell type specific) including but not limited to SP1 NFkB, or synthetic including but not limited to binding sites for tetracycline regulated trans activators tTA, rtTA, tT65, and/or rtT65; (c) one or more nucleic acid sequences from a SV40 genome, wherein the one or more sequences are obtained from a region of the SV40 genome upstream to the SV40 poly-adenylation signal; (d) a shRNA expression cassette, which encodes a shRNA directed to a host gene involved in epigenetic silencing and/or in DNA repair pathways; or (e) any combination of (a), (b), (c) and (d), wherein as compared to the parental lentivirus, the integration-defective lentiviral vector resists gene silencing.

21 Claims, 15 Drawing Sheets

Specification includes a Sequence Listing.

(56) References Cited

OTHER PUBLICATIONS

Redman et al. "Integrated Microfluidic Capillary Electrophoresis-Electrospray Ionization Devices with Online MS Detection for the Separation and Characterization of Intact Monoclonal Antibody Variants" *Analytical Chemistry* 87:2264-2272 (2015).

Suwanmanee et al. "Integration-deficient Lentiviral Vectors Expressing Codon-optimized R338L Human FIX Restore Normal Hemostasis in Hemophilia B Mice" *Molecular Therapy* 22(3):567-574 (2014).

Yanez-Munoz et al. "Effective gene therapy with nonintegrating lentiviral vectors" *Nature Medicine* 12(3):348-353 (2006) (Abstract only).

Bayer et al. "A Large U3 Deletion Causes Increased In Vivo Expression from a Nonintegrating Lentiviral Vector" Molecular Therapy, 16(12):1968-1976 (2008).

Ylisastigui et al. "Mitogen-Activated Protein Kinases Regulate LSF Occupancy at the Human Immunodeficiency Virus Type 1 Promoter" Journal of Virology, 79(10):5952-5962 (2005).

* cited by examiner

Mlu-I

```
  1 ATATACGCGTTGACATTGATTATTGACTAGTTATTAATAGTAATCAATTACGGGGTCATT  60
    ||||||||||||||||||||||||||||||||||||||||||||||||||||||||||||
  1 ATATACGCGTTGACATTGATTATTGACTAGTTATTAATAGTAATCAATTACGGGGTCATT  60

61 AGTTCATAGCCCATATATGGAGTTCCGCGTTACATAACTTACGGTAAATGGCCCGCCTGG 120
    ||||||||||||||||||||||||||||||||||||||||||||||||||||||||||||
 61 AGTTCATAGCCCATATATGGAGTTCCGCGTTACATAACTTACGGTAAATGGCCCGCCTGG 120

121 CTGACCGCCCAACGACCCCGCCCATTGACGTCAATAATGACGTATGTTCCCATAGTAAC 180
    ||||||||||||||||||||||||||||||||||||||||||||||||||||||||||||
121 CTGACCGCCCAACGACCCCGCCCATTGACGTCAATAATGACGTATGTTCCCATAGTAAC 180

181 GCCAATAGGGACTTTCCATTGACGTCAATGGGTGGACTATTTACGGTAAACTGCCCACTT 240
    ||||||||||||||||||||||||||||||||||||||||||||||||||||||||||||
181 GCCAATAGGGACTTTCCATTGACGTCAATGGGTGGACTATTTACGGTAAACTGCCCACTT 240

241 GGCAGTACATCAAGTGTATCATATGCCAAGTACGCCCCTATTGACGTCAATGACGGTAA 300
    ||||||||||||||||||||||||||||||||||||||||||||||||||||||||||||
241 GGCAGTACATCAAGTGTATCATATGCCAAGTACGCCCCTATTGACGTCAATGACGGTAA 300

301 ATGGCCCGCCTGGCATTATGCCCAGTACATGACCTTATGGGACTTTCCTACTTGGCAGTA 360
    ||||||||||||||||||||||||||||||||||||||||||||||||||||||||||||
301 ATGGCCCGCCTGGCATTATGCCCAGTACATGACCTTATGGGACTTTCCTACTTGGCAGTA 360

361 CATCTACGTATTAGTCATCGCTATTACCATGGTGATGCGGTTTTGGCAGTACATCAATGG 420
    ||||||||||||||||||||||||||||||||||||||||||||||||||||||||||||
361 CATCTACGTATTAGTCATCGCTATTACCATGGTGATGCGGTTTTGGCAGTACATCAATGG 420

421 GCGTGGATAGCGGTTTGACTCACGGGGATTTCCAAGTCTCCACCCCATTGACGTCAATGG 480
    ||||||||||||||||||||||||||||||||||||||||||||||||||||||||||||
421 GCGTGGATAGCGGTTTGACTCACGGGGATTTCCAAGTCTCCACCCCATTGACGTCAATGG 480

481 GAGTTTGTTTTGGCACCAAAATCAACGGGACTTTCCAAAATGTCGTAACAACTCCGCCCC 540
    ||||||||||||||||||||||||||||||||||||||||||||||||||||||||||||
481 GAGTTTGTTTTGGCACCAAAATCAACGGGACTTTCCAAAATGTCGTAACAACTCCGCCCC 540

541 ATTGACGCAAATGGGCGGTAGGCGTGTACGGTGGGAGGTCTATATAAGCAGCGCGTTTTG 600
    ||||||||||||||||||||||||||||||||||||||||||||||||||||||||||||
541 ATTGACGCAAATGGGCGGTAGGCGTGTACGGTGGGAGGTCTATATAAGCAGCGCGTTTTG 600

601 CCTGTACTGGGTCTCTCTGGTTAGACCAGATCTGAGCCTGGGAGCTCTCTGGCTAACTAG 660
    ||||||||||||||||||||||||||||||||||||||||||||||||||||||||||||
601 CCTGTACTGGGTCTCTCTGGTTAGACCAGATCTGAGCCTGGGAGCTCTCTGGCTAACTAG 660
```

FIGURE 1

```
 661 GGAACCCACTGCTTAAGCCTCAATAAAGCTTGCCTTGAGTGCTTCAAGTAGTGTGTGCCC 720
     ||||||||||||||||||||||||||||||||||||||||||||||||||||||||||||
 661 GGAACCCACTGCTTAAGCCTCAATAAAGCTTGCCTTGAGTGCTTCAAGTAGTGTGTGCCC 720

721 GTCTGTTGTGTGACTCTGGTAACTAGAGATCCCTCAGACCCTTTTAGTCAGTGTGGAAAA 780
     |||||||||||||||**|||||||||||||||||||||||||||||||||||||||||||
 721 GTCTGTTGTGTGACTGCGGTAACTAGAGATCCCTCAGACCCTTTTAGTCAGTGTGGAAAA 780

781 TCTCTAGCAGTGGCGCCCGAACAGGGACtTGAAAGCGAAAGGGAAACCAgagGAGCTCTC 840
     ||||||||||||||||||||||||||||||||||||||||||||||||**||||||||||
 781 TCTCTAGCAGTGGCGCCCGAACAGGGACTTGAAAGCGAAAGGGAAACCGCAGGAGCTCTC 840

841 TCGACGCAGGACTCGGCTTGCTGAAGCGCGCACGGCAAGAGGCGAGGGGCGGCGACTGGT 900
     |||||||||||||||||||||||||||||||||||||||||||||||||||||**|||
 841 TCGACGCAGGACTCGGCTTGCTGAAGCGCGCACGGCAAGAGGCGAGGGGCGGCGAGAGGT 900

901 GAGTACGCCAAAAATTTTGACTAGCGGAGGCTAGAAGGAGAGAGATGGGTGCGAGAGCGT 960
     |  |||||||||||||||||||||||||||||||||||||||||||||||||||||||||
 901 GTCTACGCCAAAAATTTTGACTAGCGGAGGCTAGAAGGAGAGAGATGGGTGCGAGAGCGT 960

961 CAGTATTAAGCGGGGGAGAATTAGATCGCGATGGGAAAAAATTCGGTTAAGGCCAGGGGG 1020
     |||||||||||||||||||||||||||||||||||||||||||||||||||||**||||
 961 CAGTATTAAGCGGGGGAGAATTAGATCGCGATGGGAAAAAATTCGGTTAAGGCCGCGGGG 1020

1021 AAAGAAAAAATATAAATTAAAACATATAGTATGGGCAAGCAGGGAGCTAGAACGATTCGC 1080
     ||||||||||||||||||||||||||||||||||||||||||||||||||||||||||||
1021 AAAGAAAAAATATAAATTAAAACATATAGTATGGGCAAGCAGGGAGCTAGAACGATTCGC 1080

1081 AGTTAATCCTGGCCTGTTAGAAACATCAGAAGGCTGTAGACAAATACTGGGACAGCTACA 1140
     ||||||||**|||||||||||||||||||||||||||||||||||||**|||||||||||
1081 AGTTAATCGCGGCCTGTTAGAAACATCAGAAGGCTGTAGACAAATAGCGGGACAGCTACA 1140

1141 ACCATCCCTTCAGACAGGATCAGAAGAACTTAGATCATTATATAATACAGTAGCAACCCT 1200
     ||||||||||||||||||||||||||||||||||||||||||||||||||||||||||||
1141 ACCATCCCTTCAGACAGGATCAGAAGAACTTAGATCATTATATAATACAGTAGCAACCCT 1200

1201 CTATTGTGTGCATCAAAGGATAGAGATAAAAGACACCAAGGAAGCTTTAGACAAGATAGA 1260
     ||||||||||||||||||||||||||||||||||||||||||||||||||||||||||||
1201 CTATTGTGTGCATCAAAGGATAGAGATAAAAGACACCAAGGAAGCTTTAGACAAGATAGA 1260

1261 GGAAGAGCAAAACAAAAGTAAGACCACCGCACAGCAA------GCGGCCGCTGATCTTCA 1314
     |||||||||||||||||||||||||||||||||||||      |||||||||||||||||
1261 GGAAGAGCAAAACAAAAGTAAGACCACCGCACAGCAATGATCAGCGGCCGCTGATCTTCA 1320
```

FIGURE 1 (Cont'd.)

```
1315 GACCTGGAGGAGGAGATATGAGGGACAATTGGAGAAGTGAATTATATAAATATAAAGTAG 1374
     |||    |||||||||||||||||||||||||||||||||||||||||||||||||||||
1321 GACGCGGAGGAGGAGATATGAGGGACAATTGGAGAAGTGAATTATATAAATATAAAGTAG 1380

1375 TAAAAATTGAACCATTAGGAGTAGCACCCACCAAGGCAAAGAGAAGAGTGGTGCAGAGAG 1434
     ||||||||||||||||||||||||||||||||||||||||||||||||||||||||||||
1381 TAAAAATTGAACCATTAGGAGTAGCACCCACCAAGGCAAAGAGAAGAGTGGTGCAGAGAG 1440

1435 AAAAAAGAGCAGTGGGAATAGGAGCTTTGTTCCTTGGGTTCTTGGGAGCAGCAGGAAGCA 1494
     |||||||||||||||||||||||||||||||||||||||||||||||||||||**||||||
1441 AAAAAAGAGCAGTGGGAATAGGAGCTTTGTTCCTTGGGTTCTTGGGAGCAGCGCGAAGCA 1500

1495 CTATGGGCGCAGCCTCAATGACGCTGACGGTACAGGCCAGACAATTATTGTCTGGTATAG 1554
     ||||||||||||||||||||||||||||||||||||||**||||||||||||**||||||
1501 CTATGGGCGCAGCCTCAATGACGCTGACGGTACAGGCCGCACAATTATTGTGCGGTATAG 1560

1555 TGCAGCAGCAGAACAATTTGCTGAGGGCTATTGAGGCGCAACAGCATCTGTTGCAACTCA 1614
     ||||||||||||||||||||||||||||||||||||||||||||||||||||||||||||
1561 TGCAGCAGCAGAACAATTTGCTGAGGGCTATTGAGGCGCAACAGCATCTGTTGCAACTCA 1620

1615 CAGTCTGGGGCATCAAGCAGCTCCAGGCAAGAATCCTGGCTGTGGAAAGATACCTAAAGG 1674
     |||| |||||||||||||||||||| |||||||| |||||||||||||||||||||||||
1621 CAGTGCGGGGCATCAAGCAGCTCCGCGCAAGAATCGCGGCTGTGGAAAGATACCTAAAGG 1680

1675 ATCAACAGCTCCTGGGGATTTGGGGTTGCTCTGGAAAACTCATTTGCACCACTGCTGTGC 1734
     |||||||||| ||||||||||||||||||| |||||||||||||||||||||||||||||
1681 ATCAACAGCTCGCGGGGATTTGGGGTTGCTGCGGAAAACTCATTTGCACCACTGCTGTGC 1740

1735 CTTGGAATGCTAGTTGGAGTAATAAATCTCTGGAACAGATCTGGAATCACACGACCTGGA 1794
     ||||||||||||||||||||||||||||| |||||||| | |||||||||||||| ||||
1741 CTTGGAATGCTAGTTGGAGTAATAAATCTGCGGAACAGATGCGGAATCACACGACGCGGA 1800

1795 TGGAGTGGGACAGAGAAATTAACAATTACACAAGCTTAATACACTCCTTAATTGAAGAAT 1854
     ||||||||||||||||||||||||||||||||||||||||||||||||||||||||||||
1801 TGGAGTGGGACAGAGAAATTAACAATTACACAAGCTTAATACACTCCTTAATTGAAGAAT 1860

1855 CGCAAAACCAGCAAGAAAAGAATGAACAAGAATTATTGGAATTAGATAAATGGGCAAGTT 1914
     |||||||| |||||||||||||||||||||||||||||||||||||||||||||||||||
1861 CGCAAAACCGCCAAGAAAAGAATGAACAAGAATTATTGGAATTAGATAAATGGGCAAGTT 1920

1915 TGTGGAATTGGTTTAACATAACAAATTGGCTGTGGTATATAAAATTATTCATAATGATAG 1974
     ||||||||||||||||||||||||||||||||||||||||||||||||||||||||||||
1921 TGTGGAATTGGTTTAACATAACAAATTGGCTGTGGTATATAAAATTATTCATAATGATAG 1980
```

FIGURE 1 (Cont'd.)

```
1975 TAGGAGGCTTGGTAGGTTTAAGAATAGTTTTTGCTGTACTTTCTATAGTGAATAGAGTTA 2034
     ||||||||||||||||||||||||||||||||||||||||||||||||||||||||||||
1981 TAGGAGGCTTGGTAGGTTTAAGAATAGTTTTTGCTGTACTTTCTATAGTGAATAGAGTTA 2040

2035 GGCAGGGATATTCACCATTATCGTTTCAGACCCACCTCCCAACCCCGAGGGGACCCGACA 2094
     ||||||||||||||||||||||||||||||||||||||||||||||||||||||||||||
2041 GGCAGGGATATTCACCATTATCGTTTCAGACCCACCTCCCAACCCCGAGGGGACCCGACA 2100

2095 GGCCCGAAGGAATAGAAGAAGAAGGTGGAGAGAGAGACAGAGACAGATCCATTCGATTAG 2154
     ||||||||||||||||||||||||||||||||||||||||||||||||||||||||||||
2101 GGCCCGAAGGAATAGAAGAAGAAGGTGGAGAGAGAGACAGAGACAGATCCATTCGATTAG 2160

2155 TGAACGGATCCA-----AAAGAAAAGGGGGGATTGGGGGGTACAGTGCAGGGGAAAGAAT 2209
     ||||||||||||     |||||||||||||||||||||||||||||||||||||||||||
2161 TGAACGGATCCATTTTAAAAGAAAAGGGGGGATTGGGGGGTACAGTGCAGGGGAAAGAAT 2220

2210 AGTAGACATAATAGCAACAGACATACAAACTAAAGAATTACAAAAACAAATTACAAAAAT 2269
     ||||||||||||||||||||||||||||||||||||||||||||||||||||||||||||
2221 AGTAGACATAATAGCAACAGACATACAAACTAAAGAATTACAAAAACAAATTACAAAAAT 2280

2270 TCAAAATTTTCGGGAGATCCCCCGGGCTGCAGGAATTCGATGGAAGATCCCCCGGGCTGC 2329
     |||||||||||||                                            |||
2281 TCAAAATTTTCGGG========================================TTA 2297

2330 AGGAATTCGATTAATAGTAATCAATTACGGGGTCATTAGTTCATAGCCCATATATGGAGT 2389
      |||||||||||||||||||||||||||||||||||||||||||||||||||||||||||
2298 ACGAATTCGATTAATAGTAATCAATTACGGGGTCATTAGTTCATAGCCCATATATGGAGT 2357

2390 TCCGCGTTACATAACTTACGGTAAATGGCCCGCCTGGCTGACCGCCCAACGACCCCCGCC 2449
     ||||||||||||||||||||||||||||||||||||||||||||||||||||||||||||
2358 TCCGCGTTACATAACTTACGGTAAATGGCCCGCCTGGCTGACCGCCCAACGACCCCCGCC 2417

2450 CATTGACGTCAATAATGACGTATGTTCCCATAGTAACGCCAATAGGGACTTTCCATTGAC 2509
     ||||||||||||||||||||||||||||||||||||||||||||||||||||||||||||
2418 CATTGACGTCAATAATGACGTATGTTCCCATAGTAACGCCAATAGGGACTTTCCATTGAC 2477

2510 GTCAATGGGTGGAGTATTTACGGTAAACTGCCCACTTGGCAGTACATCAAGTGTATCATA 2569
     ||||||||||||||||||||||||||||||||||||||||||||||||||||||||||||
2478 GTCAATGGGTGGAGTATTTACGGTAAACTGCCCACTTGGCAGTACATCAAGTGTATCATA 2537

2570 TGCCAAGTACGCCCCCTATTGACGTCAATGACGGTAAATGGCCCGCCTGGCATTATGCCC 2629
     ||||||||||||||||||||||||||||||||||||||||||||||||||||||||||||
2538 TGCCAAGTACGCCCCCTATTGACGTCAATGACGGTAAATGGCCCGCCTGGCATTATGCCC 2597
```

FIGURE 1 (Cont'd.)

```
2630 AGTACATGACCTTATGGGACTTTCCTACTTGGCAGTACATCTACGTATTAGTCATCGCTA 2689
     ||||||||||||||||||||||||||||||||||||||||||||||||||||||||||||
2598 AGTACATGACCTTATGGGACTTTCCTACTTGGCAGTACATCTACGTATTAGTCATCGCTA 2657

2690 TTACCATGGTGATGCGGTTTTGGCAGTACATCAATGGGCGTGGATAGCGGTTTGACTCAC 2749
     ||||||||||||||||||||||||||||||||||||||||||||||||||||||||||||
2658 TTACCATGGTGATGCGGTTTTGGCAGTACATCAATGGGCGTGGATAGCGGTTTGACTCAC 2717

2750 GGGGATTTCCAAGTCTCCACCCCATTGACGTCAATGGGAGTTTGTTTTGGCACCAAAATC 2809
     ||||||||||||||||||||||||||||||||||||||||||||||||||||||||||||
2718 GGGGATTTCCAAGTCTCCACCCCATTGACGTCAATGGGAGTTTGTTTTGGCACCAAAATC 2777

2810 AACGGGACTTTCCAAAATGTCGTAACAACTCCGCCCCATTGACGCAAATGGGCGGTAGGC 2869
     ||||||||||||||||||||||||||||||||||||||||||||||||||||||||||||
2778 AACGGGACTTTCCAAAATGTCGTAACAACTCCGCCCCATTGACGCAAATGGGCGGTAGGC 2837

2870 GTGTACGGTGGGAGGTCTATATAAGCAGAGCTGGTTTAGTGAACCGTCAGATCCGCTAGC 2929
     ||||||||||||||||||||||||||||||||||||||||||||||||||||||||||||
2838 GTGTACGGTGGGAGGTCTATATAAGCAGAGCTGGTTTAGTGAACCGTCAGATCCGCTAGC 2897

2930 GCTACCGGTCGCCACCATGGTGAGCAAGGGCGAGGAGCTGTTCACCGGGGTGGTGCCCAT 2989
     ||||||||||||||||||||||||||||||||||||||||||||||||||||||||||||
2898 GCTACCGGTCGCCACCATGGTGAGCAAGGGCGAGGAGCTGTTCACCGGGGTGGTGCCCAT 2957

2990 CCTGGTCGAGCTGGACGGCGACGTAAACGGCCACAAGTTCAGCGTGTCCGGCGAGGGCGA 3049
     ||||||||||||||||||||||||||||||||||||||||||||||||||||||||||||
2958 CCTGGTCGAGCTGGACGGCGACGTAAACGGCCACAAGTTCAGCGTGTCCGGCGAGGGCGA 3017

3050 GGGCGATGCCACCTACGGCAAGCTGACCCTGAAGTTCATCTGCACCACCGGCAAGCTGCC 3109
     ||||||||||||||||||||||||||||||||||||||||||||||||||||||||||||
3018 GGGCGATGCCACCTACGGCAAGCTGACCCTGAAGTTCATCTGCACCACCGGCAAGCTGCC 3077

3110 CGTGCCCTGGCCCACCCTCGTGACCACCCTGACCTACGGCGTGCAGTGCTTCAGCCGCTA 3169
     ||||||||||||||||||||||||||||||||||||||||||||||||||||||||||||
3078 CGTGCCCTGGCCCACCCTCGTGACCACCCTGACCTACGGCGTGCAGTGCTTCAGCCGCTA 3137

3170 CCCCGACCACATGAAGCAGCACGACTTCTTCAAGTCCGCCATGCCCGAAGGCTACGTCCA 3229
     ||||||||||||||||||||||||||||||||||||||||||||||||||||||||||||
3138 CCCCGACCACATGAAGCAGCACGACTTCTTCAAGTCCGCCATGCCCGAAGGCTACGTCCA 3197

3230 GGAGCGCACCATCTTCTTCAAGGACGACGGCAACTACAAGACCCGCGCCGAGGTGAAGTT 3289
     ||||||||||||||||||||||||||||||||||||||||||||||||||||||||||||
3198 GGAGCGCACCATCTTCTTCAAGGACGACGGCAACTACAAGACCCGCGCCGAGGTGAAGTT 3257
```

FIGURE 1 (Cont'd.)

```
3290 CGAGGGCGACACCCTGGTGAACCGCATCGAGCTGAAGGGCATCGACTTCAAGGAGGACGG 3349
     ||||||||||||||||||||||||||||||||||||||||||||||||||||||||||||
3258 CGAGGGCGACACCCTGGTGAACCGCATCGAGCTGAAGGGCATCGACTTCAAGGAGGACGG 3317

3350 CAACATCCTGGGGCACAAGCTGGAGTACAACTACAACAGCCACAACGTCTATATCATGGC 3409
     ||||||||||||||||||||||||||||||||||||||||||||||||||||||||||||
3318 CAACATCCTGGGGCACAAGCTGGAGTACAACTACAACAGCCACAACGTCTATATCATGGC 3377

3410 CGACAAGCAGAAGAACGGCATCAAGGTGAACTTCAAGATCCGCCACAACATCGAGGACGG 3469
     ||||||||||||||||||||||||||||||||||||||||||||||||||||||||||||
3378 CGACAAGCAGAAGAACGGCATCAAGGTGAACTTCAAGATCCGCCACAACATCGAGGACGG 3437

3470 CAGCGTGCAGCTCGCCGACCACTACCAGCAGAACACCCCCATCGGCGACGGCCCCGTGCT 3529
     ||||||||||||||||||||||||||||||||||||||||||||||||||||||||||||
3438 CAGCGTGCAGCTCGCCGACCACTACCAGCAGAACACCCCCATCGGCGACGGCCCCGTGCT 3497

3530 GCTGCCCGACAACCACTACCTGAGCACCCAGTCCGCCCTGAGCAAAGACCCCAACGAGAA 3589
     ||||||||||||||||||||||||||||||||||||||||||||||||||||||||||||
3498 GCTGCCCGACAACCACTACCTGAGCACCCAGTCCGCCCTGAGCAAAGACCCCAACGAGAA 3557

3590 GCGCGATCACATGGTCCTGCTGGAGTTCGTGACCGCCGCCGGGATCACTCTCGGCATGGA 3649
     ||||||||||||||||||||||||||||||||||||||||||||||||||||||||||||
3558 GCGCGATCACATGGTCCTGCTGGAGTTCGTGACCGCCGCCGGGATCACTCTCGGCATGGA 3617

3650 CGAGCTGTACAAGTCCGGACTCAGATCCTACTAGTAGGATCTCGAGGGATCAAGCTTATC 3709
     ||||||||||||||||||||||||||||||||||||||||||||||||||||||||||||
3618 CGAGCTGTACAAGTCCGGACTCAGATCCTACTAGTAGGATctcgagGGATCAAGCTTATC 3677

3710 GATAATCAACCTCTGGATTACAAAATTTGTGAAAGATTGACTGGTATTCTTAACTATGTT 3769
     ||||||||||||||||||||||||||||||||||||||||||||||||||||||||||||
3678 GATAATCAACCTCTGGATTACAAAATTTGTGAAAGATTGACTGGTATTCTTAACTATGTT 3737

3770 GCTCCTTTTACGCTATGTGGATACGCTGCTTTAATGCCTTTGTATCATGCTATTGCTTCC 3829
     ||||||||||||||||||||||||||||||||||||||||||||||||||||||||||||
3738 GCTCCTTTTACGCTATGTGGATACGCTGCTTTAATGCCTTTGTATCATGCTATTGCTTCC 3797

3830 CGTATGGCTTTCATTTTCTCCTCCTTGTATAAATCCTGGTTGCTGTCTCTTTATGAGGAG 3889
     ||||||||||||||||||||||||||||||||||||||||||||||||||||||||||||
3798 CGTATGGCTTTCATTTTCTCCTCCTTGTATAAATCCTGGTTGCTGTCTCTTTATGAGGAG 3857

3890 TTGTGGCCCGTTGTCAGGCAACGTGGCGTGGTGTGCACTGTGTTTGCTGACGCAACCCCC 3949
     ||||||||||||||||||||||||||||||||||||||||||||||||||||||||||||
3858 TTGTGGCCCGTTGTCAGGCAACGTGGCGTGGTGTGCACTGTGTTTGCTGACGCAACCCCC 3917
```

FIGURE 1 (Cont'd.)

3950 ACTGGTTGGGGCATTGCCACCACCTGTCAGCTCCTTTCCGGGACTTTCGCTTTCCCCCTC 4009
     ||||||||||||||||||||||||||||||||||||||||||||||||||||||||||||
3918 ACTGGTTGGGGCATTGCCACCACCTGTCAGCTCCTTTCCGGGACTTTCGCTTTCCCCCTC 3977

4010 CCTATTGCCACGGCGGAACTCATCGCCGCCTGCCTTGCCCGCTGCTGGACAGGGGCTCGG 4069
     ||||||||||||||||||||||||||||||||||||||||||||||||||||||||||||
3978 CCTATTGCCACGGCGGAACTCATCGCCGCCTGCCTTGCCCGCTGCTGGACAGGGGCTCGG 4037

4070 CTGTTGGGCACTGACAATTCCGTGGTGTTGTCGGGGAAGCTGACGTCCTTTCCATGGCTG 4129
     ||||||||||||||||||||||||||||||||||||||||||||||||||||||||||||
4038 CTGTTGGGCACTGACAATTCCGTGGTGTTGTCGGGGAAGCTGACGTCCTTTCCATGGCTG 4097

4130 CTCGCCTGTGTTGCCACCTGGATTCTGCGCGGGACGTCCTTCTGCTACGTCCCTTCGGCC 4189
     ||||||||||||||||||||||||||||||||||||||||||||||||||||||||||||
4098 CTCGCCTGTGTTGCCACCTGGATTCTGCGCGGGACGTCCTTCTGCTACGTCCCTTCGGCC 4157

4190 CTCAATCCAGCGGACCTTCCTTCCCGCGGCCTGCTGCCGGCTCTGCGGCCTCTTCCGCGT 4249
     ||||||||||||||||||||||||||||||||||||||||||||||||||||||||||||
4158 CTCAATCCAGCGGACCTTCCTTCCCGCGGCCTGCTGCCGGCTCTGCGGCCTCTTCCGCGT 4217

4250 CTTCGCCTTCGCCCTCAGACGAGTCGGATCTCCCTTTGGGCCGCCTCCCCGCATCGATAC 4309
     ||||||||||||||||||||||||||||||||||||||||||||||||||||||||||||
4218 CTTCGCCTTCGCCCTCAGACGAGTCGGATCTCCCTTTGGGCCGCCTCCCCGCATCGATAC 4277

4310 CGTCGAGACCTGGAAAAACATGGAGCAATCACAAGTAGCAACACAGCAGCTACCAATGCT 4369
     ||||||||**||||||||||||||||||||||||||||||||||||||||||||||||||
4278 CGTCGAGACGCGGAAAAACATGGAGCAATCACAAGTAGCAACACAGCAGCTACCAATGCT 4337

4370 GCTTGTGCCTGGCTAGAAGCACAAGAGGAGGAGGAGGTGGGTTTTCCAGTCACACCTCAG 4429
     ||||||||**||||||||||||||||||||||||||||||||||**||||||||||||||
4338 GCTTGTGCGCGGCTAGAAGCACAAGAGGAGGAGGAGGTGGGTTTTCCGCTCACACCTCAG 4397
                                                                    ← AP4

4430 GTACCTTTAAGACCAATGACTTACAAGGCAGCTGTAGATCTTAGCCACTTTTTAAAAGAA 4489
     ||||||||||||||||||||||||||||||**||||||||||||||||||||||||||||
4398 GTACCTTTAAGACCAATGACTTACAAGGCAGCGCTAGATCTTAGCCACTTTTTAAAAGAA 4457

FIGURE 1 (Cont'd.)

```
4490 AAGGGGGGACTGGAAGGGCTAATTCACTCCCAACGAAGACAAG---------------- 4532
     |||||||||||||||||||||||||||||||||||||||||||
4458 AAGGGGGGACTGGAAGGGCTAATTCACTCCCAACGAAGACAAGCCCGGGCATAAAATGAA 4517
```

SV40 3f46 opposite orientation

```
4532 ------------------------------------------------------------ 4532

4518 TGCAATTGTTGTTGTTAACTTGTTTATTGCAGCTTGACTAGAGTCAATAATGGTTACAAA 4577
```

SV40 2f2R opposite orientation

```
4533 --------------------------------------------ATATC--------- 4537
                                                 |||||
4578 TAAAGCAATAGCATCACAAATTTCACAAATAAAGCATTTTTTTCACGATATCGAGCTTGC 4637
```

In grey SV40 USE opposite orientation

```
4538 --------------------------------------CACTGACCGCAC-GCCTGC 4555
                                          |||||||||||| ||||||
4638 TACAAGGGACTTTCCGCTGGGGACTTTCCAGGGAGGCGTGGCCTGGGCGGGACTGGGGAG 4697
```

2XNFkB                        AP4              3XSP1

```
4556 AGGCTAGCCCTCAGATCCTGCATATAAGCAGCTGCTTTTTGCCTGTACTGGGTCTCTCTG 4615
     ||||||||||||||||  || | |||||||**|||||||||*|||||||||||||||||
4698 TGGCGAGCCCTCAGAT===GC=T=GCAGCAGCGCCTTTTTGCTTGTACTGGGTCTCTCTG 4752

4616 GTTAGACCAGATCTGAGCCTGGGAGCTCTCTGGCTAACTAGGGAACCCACTGCTTAAGCC 4675
     ||||||||||||||||||||||||||||||||||||||||||||||||||||||||||||
4753 GTTAGACCAGATCTGAGCCTGGGAGCTCTCTGGCTAACTAGGGAACCCACTGCTTAAGCC 4812

4676 TCAATAAAGCTTGCCTTGAGTGCTTCAAGTAGTGTGTGCCCGTCTGTTGTGTGACTCTGG 4735
     ||||||||||||||||||||||||||||||||||||||||||||||||||||||||||||
4813 TCAATAAAGCTTGCCTTGAGTGCTTCAAGTAGTGTGTGCCCGTCTGTTGTGTGACTCTGG 4872

4736 TAACTAGAGATCCCTCAGACCCTTTTAGTCAGTGTGGAAAATCTCTAGCAGGGCCCGTTT 4795
     ||||||||||||||||||||||||||||||||||||||||||||||||||||||||||||
4873 TAACTAGAGATCCCTCAGACCCTTTTAGTCAGTGTGGAAAATCTCTAGCAGGGCCCGTTT 4932

4796 AAAC 4799  pTK945
     ||||               ← Pme-I
4933 AAAC 4936  pTK1759
```

In bold black letters. Right orientation

3F46 region I
Located upstream to the SV40 pA SV40

In grey letters. Right orientation

2F2R region II
Located upstream to the SV40 pA SV40

5'aagctgcaataaacaagttaacaacaaacaattgcattcatttatgGCTAGATAA*agtgaaaaaatgctttatttgtgaaatttatatatctat tactttattgtgccattat* 3'

Underlined italic letters (in region II) are part of the Upstream Elements (USE)

B

In bold black letters region I (3f46).
Opposite orientation

In grey letters region II (2F2R).
Opposite orientation

5'ccccgggcataaaatgaatgcaatgttgttgttaacttgtttattgcaGCTTgactagagtcA*ataaagttacaaataaagcaatagcatcaca aattcacaataaagcattttcac*GatatC 3'

Figure 2

METHODS AND COMPOSITIONS FOR INTEGRATION DEFECTIVE LENTIVIRAL VECTORS

STATEMENT OF PRIORITY

This application is a 35 U.S.C. § 371 national phase application of International Application Ser. No. PCT/US2016/057,041, filed Oct. 14, 2016, which claims the benefit, under 35 U.S.C. § 119(e), of U.S. Provisional Patent Application No. 62/241,986, filed Oct. 15, 2015, the disclosure of each of which is incorporated herein by reference in their entirety.

STATEMENT OF GOVERNMENT INTEREST

The present invention was made with government support under Grant No. R01-DK058702-10 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-742 ST25.txt, 13,886 bytes in size, generated on Apr. 11, 2018 and filed via EFS-Web, is provided in lieu of a paper copy. This Sequence Listing is incorporated by reference into the specification for its disclosures.

FIELD OF THE INVENTION

The presently disclosed subject matter pertains to integration-defective lentiviral vectors and methods for making and using the same, such as in gene therapy and in basic biology research.

BACKGROUND OF THE INVENTION

The capacity to introduce a particular foreign or native gene sequence into a cell and to control the expression of that gene is of value in the fields of medicine and biological research. Such capacity has a wide variety of useful applications, including but not limited to studying gene regulation and designing a therapeutic basis for the treatment of disease.

The introduction of a particular foreign or native gene into a host cell can be facilitated by introducing a gene sequence into a suitable nucleic acid vector. A variety of methods have been developed that allow the introduction of such a recombinant vector into a desired host cell. The use of viral vectors can result in the rapid introduction of the recombinant molecule into a wide variety of host cells.

Lentiviruses are a subgroup of retroviruses that are capable of infecting non-dividing cells. These viruses include, but are not limited to, HIV-1, HIV-2, SIV, EIAV, and FIV. Lentiviruses possess gag, pol, and env genes in addition to other accessory genes that are flanked by two long terminal repeat (LTR) sequences.

Integration defective lentivirus vectors (IDLVs) have been produced by introducing combinations of mutations that disable the integrase protein itself or to alter the integrase recognition sequences (att) in the viral LTR (see e.g., Yanez-Munoz et al. (2006) Nat Med 12(3):348-353; Nightingale et al. (2006) Mol Ther 13(6):1121-1132). Recent in vitro and in vivo studies show that IDLVs can mediate stable transduction in non-dividing cells and allow for measurable levels of transgene expression (see e.g., Yanez-Munoz et al. (2006) Nat Med 12(3):348-353; Nightingale et al. (2006) Mol Ther 13(6):1121-1132); Suwanmannee et al. (2014) Mol Ther 22(3):567-74. Therefore, the high efficiency of gene transfer mediated by lentiviruses can be harnessed in vivo without a requirement for vector integration. This reduces the likelihood of insertional mutagenesis associated with integrating vectors. In addition, IDLVs can be used as to transiently express potentially genotoxic proteins (e.g., zinc finger nucleases, Cas9, Talens) in dividing cells. However, transcriptional silencing of lentiviruses can significantly reduce IDLV transgene expression levels, thereby reducing their efficacy and usage.

SUMMARY OF THE INVENTION

This summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In accordance with some embodiments of the presently disclosed subject matter, provided herein is an integration-defective lentiviral vector based on a parental lentivirus. In some embodiments, the integration-defective lentiviral vector comprises one or more of the following:
 (a) a mutation, deletion or other modification of one or more binding sites for a host factor involved in gene silencing;
 (b) addition of binding site(s) for a transcription activator natural (such as but not limited to ubiquitous and/or tissue/cell type specific) including but not limited to SP1 NFkB or synthetic including but not limited to binding sites for tetracycline regulated trans activators tTA, rtTA, tT65, and/or rtT65;
 (c) one or more nucleic acid sequences from a SV40 genome, wherein the one or more sequences are obtained from a region of the SV40 genome upstream to the SV40 poly-adenylation signal either in the same or opposite orientation to the LTRs;
 (d) a shRNA expression cassette, which encodes a shRNA directed to a host gene involved in epigenetic silencing or in proteasome activity; or
 (e) any combination of (a), (b), (c) and (d),
 wherein as compared to the parental lentivirus, the integration-defective lentiviral vector resists gene silencing.

In some embodiments, the one or more binding sites for a host factor are selected from the group including but not limited to an AP-4 binding site, a LSF1 binding site, and the majority of the 3' U3 region including the NRE; and any combination of any of the foregoing. In some embodiments, the lentiviral vector comprises a mutation introduced at one or more of the deleted binding sites to retain a secondary structure in the nucleic acid sequence of the vector. In some embodiments, the shRNA expression cassette is directed to a host gene involved in epigenetic silencing selected from the group including but not limited to AP4, p300, YY1, LSF1, HDACs, histone methylases, histone sumolating, histone phosphorating, proteins involved with the PRC1 or PRC2 complexes, BMI, Ring1B). In some embodiments, the shRNA expression cassette is controlled by PolIII promoters including but not limited to the U6 and the H1 promoters, or by a PolII promoter or as transfected (using various methodologies of transfected) siRNAs directed to the target genes. In some embodiments, the lentiviral vector comprises a heterologous sequence. In some embodiments, the heterologous sequence is selected from the group comprising one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity, sequences that encode genome-editing proteins (e.g., CAS9, guide RNAs, zinc-finger-nucleases, TALENs, etc.) and de-differentiation factors to generate iPS and combinations thereof. In some embodiments, the marker genes are selected from the group consisting of β-galactosidase gene, hygromycin gene, blastocidin gene, MGMT gene, neomycin gene, puromycin gene, cytosine deaminase gene, secreted alkaline phosphatase gene, fluorescent protein genes, and combinations thereof.

A method of conditioning target cells to enhance IDLV transduction is also provided. In some embodiments, the method comprises: delivering a shRNA expression cassette encoding a shRNA directed to a host gene involved in host protein ubiquitination and proteasome activity epigenetic silencing; a siRNA directed to a host gene involved in host protein ubiquitination and proteasome activity pathways to target cells at the time of or prior to IDLV transduction; and/or delivering a small molecule inhibitor of host proteasome activity, including but not limited to a Velcade and/or MG-132, at the time of or prior to IDLV transduction. A method of conditioning target cells to enhance IDLV transduction is also provided.

In some embodiments, the method comprises: delivering an expression cassette encoding hyperthermia induced proteins, or mRNAs encoding hyperthermia induced proteins, or hyperthermia induced proteins, including but not limiting to heat shock proteins HSP90AA1 (Hsp90alpha), HSP90AB1 (HSP90beta), HSPA1A (Hsp70-1), HSPA8 (HSC70/71), DNAJB1 (Hsp40), HSCB (Hsc20), HSPB1 (Hsp27), HSPD1 (GroEL, Hsp60), HSPE1 (GroES, Hsp10), TriC, and Heat-shock factor 1 (HSF1).

In some embodiments the method comprises employing an IDLV in accordance with the presently disclosed subject matter, a separate gene delivery system, or a combination thereof, to deliver the shRNA expression cassette. In some embodiments, the above methods directed to inhibit host protein ubiquitination and proteasome activity will be combined with methods directed to inhibit epigenetic silencing either by shRNA, siRNA or small molecules directed to host genes/proteins involved in epigenetic silencing including but not limited to AP4, p300, YY1, LSF1, HDACs, histone methylases, histone sumolating, histone phosphorating, proteins involved with the PRC1 or PRC2 complexes, BMI, Ring1B).

Also provided is an isolated nucleic acid molecule, comprising one or more of the following:
(a) a mutation, deletion or other modification of one or more binding sites for a host factor involved in gene silencing;
(b) addition of a binding site for a transcription activator preferably but not limited to an NFkB binding site and/or SP1 binding site to the 3' U3 region of the nucleic acid molecule.
(c) one or more nucleic acid sequences from a SV40 genome, wherein the one or more sequences are obtained from a region of the SV40 genome upstream to the SV40 poly-adenylation signal either in the same or opposite orientation to the LTR;
(d) a shRNA expression cassette, which encodes a shRNA directed to a host gene involved in epigenetic silencing; or
(e) any combination of (a), (b), (c) and (d); and optionally comprising a heterologous nucleotide sequence, one or two retroviral long terminal repeats (LTRs), a packaging signal, with or without a rev responsive element and a eukaryotic promoter with or without a functional polypurine tract (PPT).

In some embodiments, the nucleic acid can comprise a viral origin of replication or a sequence that can directly or indirectly mediate replication of the nucleic acid molecule by a host. In some embodiments, the nucleic acid can comprise a bacterial origin of replication and a bacterial selection marker situated between the two LTRs. In some embodiments, the viral origin of replication is selected from the group comprising Epstein-Barr Virus OriP and an SV40 origin of replication. In some embodiments, the sequence that can directly or indirectly mediate replication of the vector nucleic acid by the host cell is selected from the group comprising (a) a sequence recognized by the host-cell replication machinery; (b) a sequence encoding a protein that can associate with and/or modulate host-cell replication machinery; (c) a sequence encoding a protein that can associate with the protein of part (b) or can recognize a sequence of the nucleic acid molecule and (d) a combination of (a)-(c) with a viral origin of replication. In some embodiments, the nucleic acid can comprise a post-transcriptional regulatory element.

A vector comprising a nucleic acid molecule as disclosed herein is also provided. In some embodiments, the vector comprises only a single (one) LTR. In some embodiments, the vector comprises a self-inactivating deletion in the U3 region of the LTR. In some embodiments, the deleted portion of the U3 region is replaced with an inducible promoter. In some embodiments, the vector comprises a site-directed recombination site. In some embodiments, the vector comprises a sequence that encodes a cis element that provides for cross-packaging of the vector in a viral particle. In some embodiments, the vector comprises a deleted or non functional 3' PPT.

A recombinant retroviral particle comprising a vector as disclosed herein is also provided. In some embodiments, the recombinant retroviral particle is for use in gene therapy. In some embodiments, a retroviral provirus produced by infection of target cells with the recombinant retroviral particle is provided, as is mRNA of the retroviral provirus and/or RNA of the retroviral provirus.

An inducible retroviral vector packaging cell line comprising a retroviral vector as disclosed herein and at least one construct encoding one or more proteins required for the retroviral vector to be packaged is also provided. A retroviral vector kit comprising: an integration-defective or integration competent lentiviral vector transfer cassette as disclosed herein; a packaging cell line comprising a packaging cassette expressing a non-functional integrase protein including but not limited to mutations in one or more integrase amino acids D64, D115 E152, N120, W235, R262, R263, K264, and a packaging cell line comprising at least one construct encoding one or more proteins required for the viral vector to be packaged, is also provided.

Also provided is a method of producing integration-defective vector particles, comprising transfecting a packaging cell line with an integration-defective or integration competent retroviral vector transfer cassette as disclosed herein, wherein the packaging cell line provides proteins for the retroviral vector to be packaged and wherein the packaging cell line expresses an integration defective integrase mutant.

Thus, a method is provided herein of producing integration-defective vector particles, comprising transfecting a packaging cell line with an integration-defective retroviral vector of this invention in a transfer cassette, wherein the packaging cell line provides an envelope protein as well as proteins for the retroviral vector to be packaged, uncoated, reverse-transcribed, and nuclear imported including integration-defective integrase. The proteins provided by the packaging cell line can be encoded by expression cassettes which are either stably incorporated into the packaging cell line chromatin and/or by expression of packaging cassettes that are transiently transfected.

Additionally provided herein is a method of producing integration-defective vector particles, comprising transfecting a packaging cell line with an integration-defective retroviral vector or an integration competent vector of this invention in a transfer cassette, wherein the packaging cell line provides an envelope protein as well as proteins for the retroviral vector to be packaged, uncoated, reverse-transcribed, and nuclear imported including integration-defective integrase. The proteins provided by the packaging cell line can be encoded by expression cassettes which are either stably incorporated into the packaging cell line chromatin and/or by expression packaging cassettes that are transiently transfected.

Also provided is a method for expressing a nucleotide sequence of interest in a cell of an animal without integration of the nucleotide sequence into the animal's genome, the method comprising infecting one or more cells with the integration-defective retroviral particle as disclosed herein.

A method for inserting a nucleotide sequence of interest into a host cell genome in a site-specific manner is also provided. In some embodiments, the method comprises:
   (a) transducing a compatible host cell with the integration-defective vector as disclosed herein comprising in operable combination the nucleotide sequence of interest and one or more site-directed recombination sequences; and
   (b) transfecting or transducing the compatible host cell with a nucleic acid comprising a sequence encoding a nuclease or recombinase that can mediate site-specific integration at the recombination sequence, wherein the transfecting or transducing of part (b) can occur separately or in the same step as part (a),
   (c) wherein the nucleotide sequence of interest is inserted in a site-specific manner into the host cell genome.

In some embodiments, the transfecting or transducing of part (b) occurs in the same step as part (a) and the nucleic acid comprising a sequence encoding a nuclease or recombinase is the integration-defective vector of part (a). In some embodiments, the transfecting or transducing of part (b) occurs in the same step as part (a) and the nucleic acid comprising a sequence encoding a nuclease or recombinase is a separate vector, plasmid, or nucleic acid molecule than the integration-defective vector of part (a).

A method for inserting a nucleotide sequence of interest into a host cell genome in a non-specific manner is also provided. In some embodiments the method comprises:
   (d) transducing a host cell with the integration-defective vector as disclosed herein, comprising in operable combination, the nucleotide sequence of interest and one or more transposon sequences; and
   (e) transfecting or transducing the host cell with a nucleic acid comprising a sequence encoding a transposase that can mediate integration into the host genome, wherein the transfecting or transducing of part (b) can occur separately or in the same step as part (a),
   (f) wherein the nucleotide sequence of interest is inserted into the host cell genome.

In some embodiments, the transfecting or transducing of part (b) occurs in the same step as part (a) and the nucleic acid comprising a sequence encoding a transposase is the integration-defective vector of part (a). In some embodiments, the transfecting or transducing of part (b) occurs in the same step as part (a) and the nucleic acid comprising a sequence encoding a transposase is a separate vector, plasmid or nucleic acid molecule than the integration-defective vector of part (a).

The present invention further encompasses any and all constructs, vectors, compositions, methods, devices, systems, apparatuses, and/or uses shown and/or described expressly or by implication in the information provided herein, including but not limited to features that may be apparent and/or understood by those of skill in the art.

It is an object of the presently disclosed subject matter to provide integration-defective lentiviral vectors and related methods that provide for a reduction in transcriptional silencing.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 1: Sequence alignment of conventional lentiviral vector pTK945 (SEQ ID NO:1) and the silencing-resistant pTK1759 (SEQ ID NO:2). The sequence of both vectors (pTK945 and pTK1759) starts at the 5' CMV promoter (4 base pairs upstream to the Mlu-I restriction site) and ends downstream to the 3 LTR at the Pme-I restriction site. The mutations that render pTK1759 silencing resistant, including mutations in the LSF-I and the AP-4 sites, are boxed. The three SP-1 and two NFkB sites, which were incorporated into the 3' LTR in pTK1759 are shown. The SV40 sequences which were incorporated in opposite orientation to the 3' LTR in pTK1759 are shown.

FIG. 2: The sequence of the two regions (region I in bold black lower case and region II in grey lower case) upstream to the SV40 LTR. A. The sequence (5' to 3', SEQ ID NO:3) in the same orientation as the SV40 and the HIV-1 vector LTRs. The USE in region II is underlined. B. The sequence (5' to 3', SEQ ID NO:4) of the same two regions in opposite orientation to the HIV-1 vector LTRs.

pTK113: A self inactivating HIV-1 based vector devoid of TATA box, the NFkB, and the SP1 binding sites in the U3 region.

pTK1489: A self inactivating HIV-1 based vector devoid of the negative regulatory element, the NFkB-, the SP1-binding site in the U3 region. Devoid of two AP4 binding sites (one in the U3 region and the second upstream to the 3' U3). Contains one sequence from the SV40 poly-adenylation (pA) site region (does not contain the pA site itself.

pTK1672: A self inactivating HIV-1 based vector devoid of the negative regulatory element site and the TATA-box in the U3 region. Devoid of two AP4 binding sites (one in the U3 region and the second upstream to the 3' U3). Contains two sequences from the SV40 poly-adenylation (pA) site region (does not contain the pA site itself.

pTK1591: A self inactivating HIV-1 based vector devoid of the negative regulatory element, the NFkB-, the SP1-binding site in the U3 region. Devoid of two AP4 binding sites (one in the U3 region and the second upstream to the 3' U3). Contains one sequence from the SV40 poly-adenylation (pA) site region (does not contain the pA site itself). Devoid of LSF1 sites.

pTK1678: A self inactivating HIV-1 based vector devoid of the negative regulatory element, the NFkB-, the SP1-binding site in the U3 region. Devoid of two AP4 binding sites (one in the U3 region and the second upstream to the 3' U3). Contains one sequence from the SV40 poly-adenylation (pA) site region (does not contain the pA site itself). Devoid of LSF1 sites, including the LSF1 in the parental splice donor (SD).

pTK1682: A self inactivating HIV-1 based vector devoid of the negative regulatory element, and the TATA box in the U3 region. Devoid of two AP4 binding sites (one in the U3 region and the second upstream to the 3' U3). Contains two sequences from the SV40 poly-adenylation (pA) site region (does not contain the pA site itself). Devoid of LSF1 sites, including the LSF1 in the parental SD.

Figure 4:
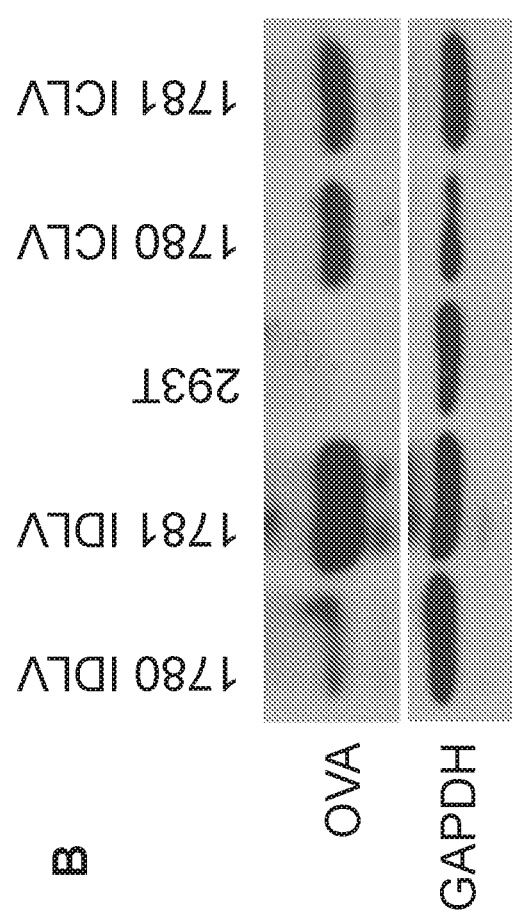

FIG. 4: Enhanced episomal expression of chicken ovalbumin from the silencing resistant lentiviral vector pTK1781. pTK1780 and pTK1781 are self inactivating lentiviral vectors expressing the codon optimized ovalbumin cDNA under the control of a CMV promoter. pTK1780 is a conventional lentiviral vector. pTK1781 contains all LSF1 and AP4 mutations and a modified U3 region with the two SV4 sequences in opposite orientation to the LTRs. ICLV and IDLV particles were generated by transient transfection in 293T cells using the VSV-G envelope expression cassette, and HIV-1 packaging cassettes expressing WT-integrase or integrase mutant (Delta-NRF or pTK939, respectively). A) Titer of physical vector particles was determined by p24gag ELISA. B) 293T cells in a 6-well plate were transduced with 20 ul of either pTK1780 or pTK1781 ICLV/IDLV (described in A). The cells were harvested at 48 hr post infection. Cell lysates (10 microgram protein) were analyzed for chicken ovalbumin expression by western blotting. GAPDH expression was used as loading control. Cell lysate of 293T cells served as a negative control.

Figure 5:
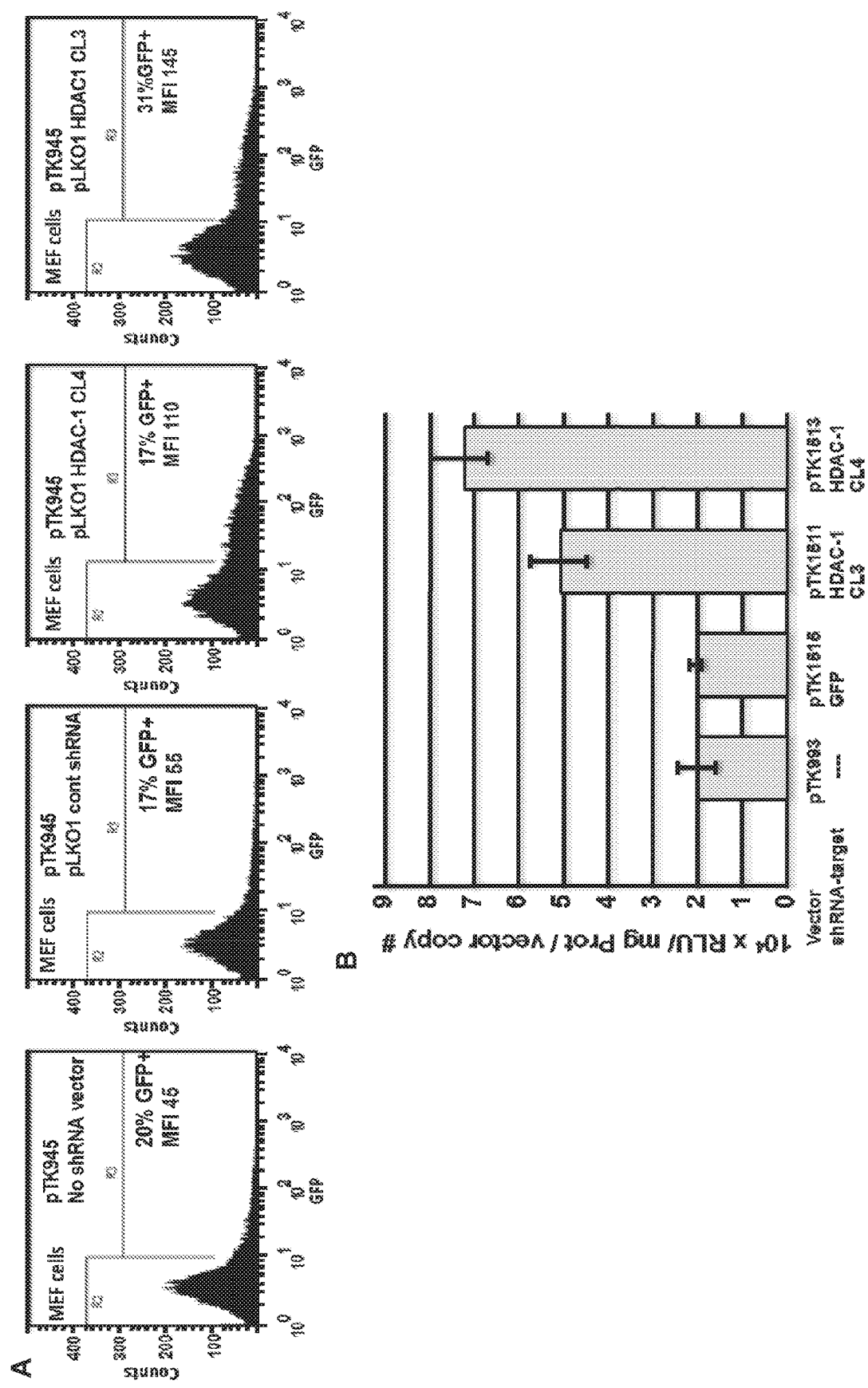

FIG. 5: Enhancing IDLV expression with HDAC-directed shRNAs. (A). FACscan analysis of MEF re-transduced with GFP-expressing IDLV (pTK945) two days after transduction with pLKO1 vectors carrying HDAC-1 directed shRNAs. As shown, IDLV expression was enhanced by an earlier transduction with shRNA clones 3 and 4 as compared to MEF cells either not transduced with a pLKO1 vector or transduced with a pLKO1 vector expressing a control irrelevant shRNA. (B) Incorporation of HDAC-1 and directed shRNA expression cassettes into IDLVs (pTK1511, pTK1513) enhanced luciferase expression. Note that luciferase expression was normalized by vector copy number. No enhancement of IDLV expression was observed from an IDLV carrying the control GFP-directed shRNA (pTK1515).

Figure 6:
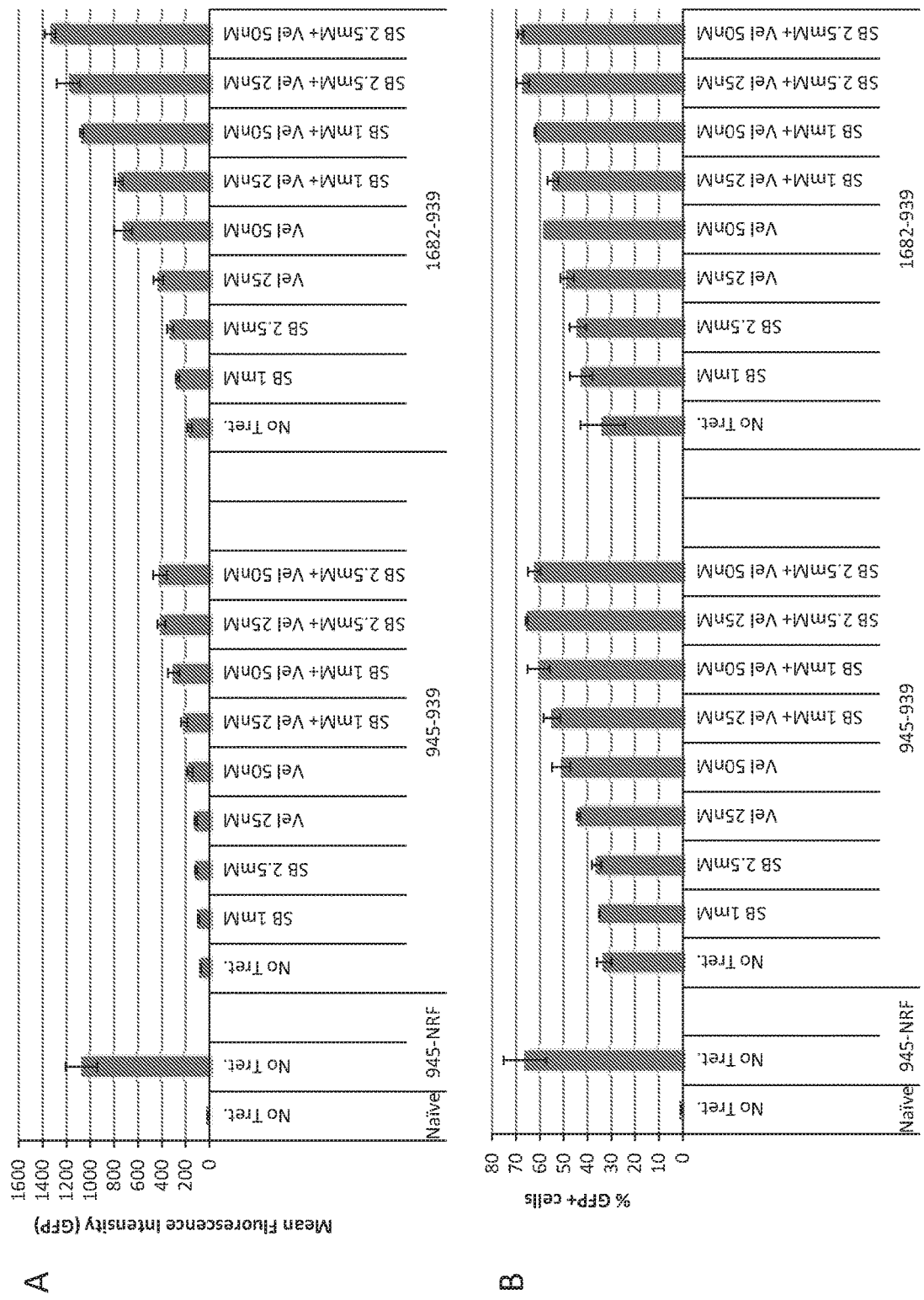

FIG. 6: Vector expression following sodium butyrate and Velcade treatment at 60 hours post infection (15 hours of drug treatment). Proteasome and HDAC inhibitors (Velcade and sodium butyrate, respectively) enhance IDLV transduction of 293T cells. A) Levels of GFP expression in 293T cells transduced with IDLVs (vTK945 or vTK1862) either in the presence or absence of the Velcade (25 mM or 50 mM) and sodium butyrate (1 mM or 2.5 mM), and their combination was determined by FACscan analysis. B) The effect of the above treatments on the percentage of GFP expressing cells. Note the unexpected synergistic effect of combining sodium butyrate and Velcade treatment on IDLV expression.

Figure 7:
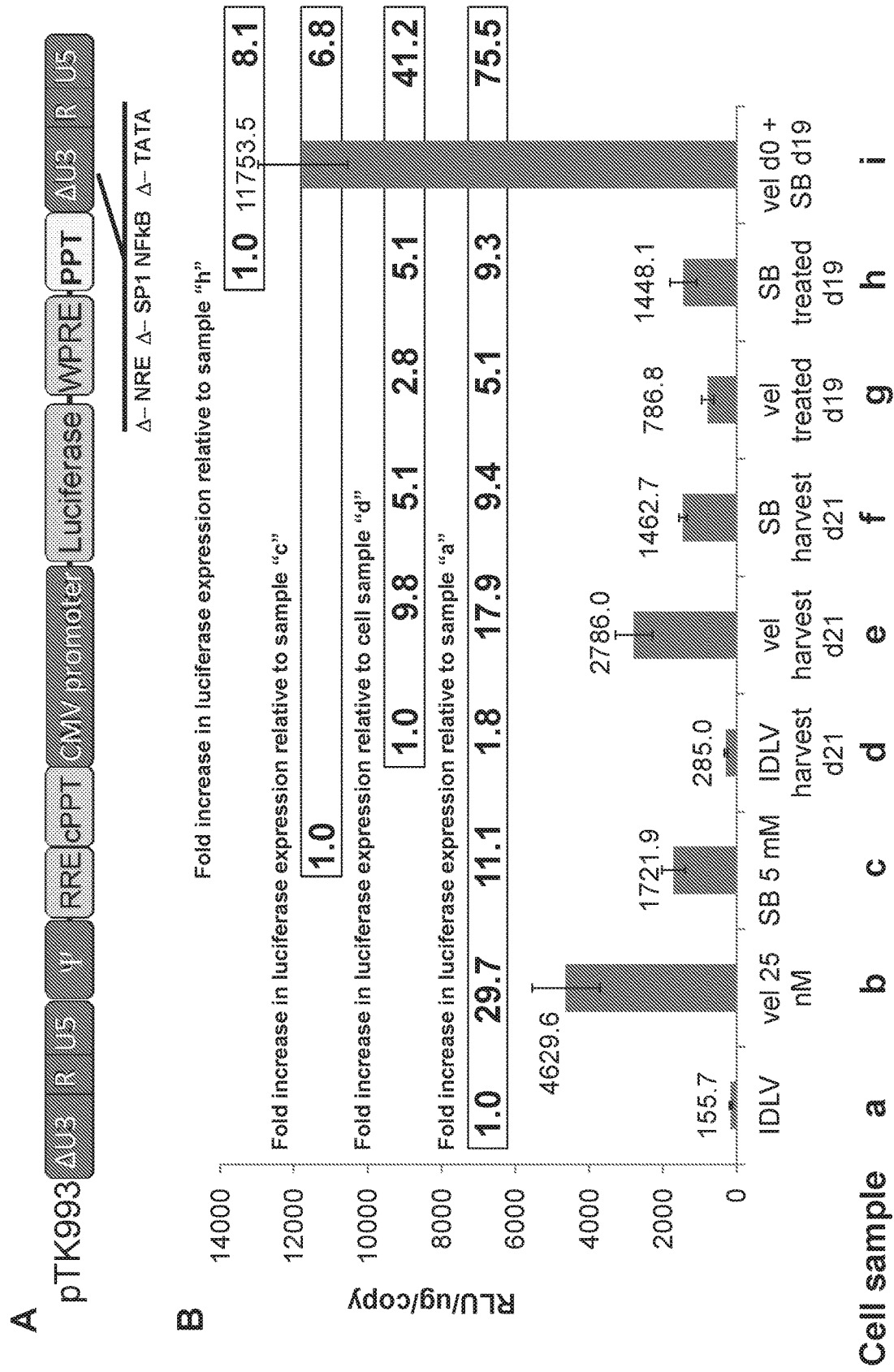

FIG. 7: A short-term treatment of host cells with proteasome inhibitor (velcade) at the time of IDLV transduction results in long-term sensitivity of IDLV expression to HDAC inhibitor (sodium butyrate) treatment. A) Depiction of a conventional self-inactivating HIV-1 vector (pTK993) from which the firefly luciferase is expressed under the control of a CMV promoter. Note that the U3 region of the above vector is deleted of the negative regulatory element (NRE), it does not contain SP1 and NFkB site and it is devoid of a TATA box. B) To characterize the short- and long-term effects of HDAC and proteasome inhibitors on IDLV gene expression, human embryo fibroblasts (HEFs) were transduced with IDLV carrying the firefly luciferase cDNA under the control of a CMV promoter. HEF transduction was carried out either in the absence (samples a, d, g and h) or in the presence of Velcade (25 nM) for 24 hours (samples b, e and i) or sodium butyrate (5 mM) for 48 hours (samples c and f). At day 19 post transduction, sample g was treated with Velcade (25 nM) for 24 hours, while samples h and i were treated with sodium butyrate (5 mM) for 48 hours. Cell samples were harvested at either 48 hours (samples a-c) or 21 days post-transduction and analyzed for luciferase expression, which was normalized to protein content and vector copy number per diploid cell genome (VCN). The readout of normalized luciferase expression is shown above each sample. The fold of increase in IDLV expression of treated sample cells relative to specific sample-control is shown in bold letters. Most importantly, the data obtained from sample i demonstrated an unexpected long-term effect (a 75-fold increase) of short-term Velcade treatment on HDAC inhibitor (sodium butyrate)-mediated enhancement of IDLV expression at 21 days post transduction.

DETAILED DESCRIPTION OF THE INVENTION

The present subject matter will now be described more fully hereinafter with reference to representative embodiments of the presently disclosed subject matter. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Integration-defective lentiviral vectors (IDLVs) efficiently ferry large genetic cargos to dividing and non-dividing cells in vitro and in vivo. The IDLV genome is stable in non-dividing or slowly dividing cells. Thus, in these cells IDLVs maintain long-term gene expression. In dividing cells the presence of IDLVs lacking origin of replication is transient. This property can be employed to transiently express potentially cellular- and geno-toxic proteins whose biological functions are required for a short time. These include but are not limited to: genome-editing proteins (CAS9, Zinc-finger-nucleases, TALENs) and de-differentiation factors to generate iPS. Although IDLVs are promising, transcriptional silencing of IDLVs can significantly reduce their efficacy and their usage. Disclosed herein is the development of IDLVs that exhibit improved gene expression as well as a methodology for inhibiting the epigenetic silencing mechanism in IDLV transduced cells.

IDLVs reduce the likelihood of insertional mutagenesis and provide transient gene expression of toxic genes in dividing cells. In addition IDLVs efficiently transduce target tissues in vivo as well as stem cells (is and ES), primary human cells, and hematopoietic stem cells in vitro. IDLVs are currently used for vaccination and for immunotherapy application. Low level of transgene expression from IDLVs reduces their efficacy and usage as a delivery vehicle to express gene products involved in genetic editing. The presently disclosed subject matter addresses these limitations and thus, can be employed in genetic editing (CRISPR, TALEN, Zinc-Finger Nucleases), and immune therapy, for example.

I. Definitions

It is to be understood that the terminology used herein is for the purpose of describing particular embodiments only and is not intended to be limiting. Unless defined otherwise, all technical and scientific terms used herein have the same meaning as commonly understood to one of ordinary skill in the art to which the presently disclosed subject matter belongs. Although any methods and materials similar or equivalent to those described herein can be used in the practice or testing of the presently disclosed subject matter, representative methods and materials are herein described. All publications, patent applications, patents, and other references mentioned herein are incorporated by reference herein in their entirety.

Following long-standing patent law convention, the terms "a," "an," and "the" refer to "one or more" when used in this application, including in the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about" as used herein when referring to a measurable value such as an amount of weight, time, dose, etc., is meant to encompass variations of in some embodiments±20%, in some embodiments±10%, in some embodiments±5%, in some embodiments ±1%, and in some embodiments±0.1% from the specified amount, as such variations are appropriate to perform the disclosed methods and/or employ the disclosed compositions.

As used herein, the term "cis-regulatory element" or "cis-element" has the same meaning as commonly understood to one of ordinary skill in the art; i.e., is a region of DNA or RNA which regulates the expression of genes located on that same strand of DNA or RNA.

As used herein, the term "construct" can be used in reference to nucleic acid molecules that transfer DNA segment(s), RNA segment(s), or combinations thereof from one cell to another. The term "vector" can be used interchangeably with "construct".

The term "gene therapy" as used herein refers to a general method for treating a pathologic condition or to enhance desired gene function in a subject by inserting an exogenous nucleic acid into an appropriate cell(s) within the subject. The nucleic acid is inserted into the cell in such a way as to maintain its functionality, e.g., maintain the ability to express a particular polypeptide. In certain cases, insertion of the exogenous nucleic acid results in the expression of a therapeutically effective amount of a particular polypeptide.

The term "heterologous" when used with reference to a nucleic acid indicates that the nucleic acid comprises one or more subsequences that are not found in the same relationship to each other in nature. For instance, the nucleic acid can be recombinantly produced, having two or more sequences from unrelated genes arranged to make a new functional nucleic acid. For example, in some embodiments, the nucleic acid has a promoter from one gene arranged to direct the expression of a coding sequence from a different gene. Thus, with reference to the coding sequence, the promoter is heterologous. The term "heterologous" can also be used to refer to a nucleic acid that is not native to a host cell. In some embodiments herein, the term "heterologous nucleotide sequence" is used interchangeably with "nucleotide sequence of interest".

"Isolated", as used herein, means that a naturally occurring nucleic acid sequence, DNA fragment, DNA molecule, coding sequence, or oligonucleotide is removed from its natural environment, or is a synthetic molecule or cloned product.

An "LTR" is a long terminal repeat. LTRs are sequences found at the ends of retroviruses. The sequence in the LTR which interacts with the viral integrase is sometimes called att sequence, for attachment. Inside the LTRs reside three distinct subregions: U3 (the enhancer and promoter region, transcribed from the 3'-LTR), R (repeated at both ends of the RNA), and U5 (transcribed from the 5'-LTR). The LTRs and additional sequences flanked by the LTRs, including the primer binding sites (PBS), splice sites, packaging signal, rev response element (RRE) central and 3' polypurine tracts (cPPT and 3' PPT)), comprise the cis-acting sequences of a retroviral vector. Sources of LTR nucleic acid sequences and other cis elements, e.g., nucleic acid fragments or segments, include, but are not limited to murine retroviruses, murine VL30 sequences, retrotransposons, simian retroviruses, avian retroviruses, feline retroviruses, lentiviruses, avian retroviruses and bovine retroviruses, foamy viruses.

The terms "non-integrating" and "integration-deficient" are used interchangeably herein to describe the viral vectors and viral particles of the presently disclosed subject matter.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. The terms "nucleic acid", "nucleotide sequence", and "polynucleotide sequence" are herein used interchangeably.

The term "operable combination" refers to a functional arrangement of two or more different nucleic acid sequences wherein their physical proximity to each other results in one or more of the different nucleic acid sequences influencing an activity and/or a behavior of another of the different nucleic acid sequences. In some embodiments, a nucleotide sequence of interest is in operable combination with one or more site-directed recombination sequences. In such embodiments, the nucleotide sequence of interest can be integrated into a desired location in a nucleic acid by operation of a nuclease or recombinase on the one or more site-directed recombination sequences.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "packaging cassette" encodes components necessary for production of viral particles by a cell transduced by the packaging vector. The packaging cassette optionally includes all of the components necessary for production of viral particles, or optionally includes a subset of the components necessary for viral packaging and transduction including uncoating, reverse-transcription (resulting in either linear or circular double-stranded viral/vector genome), nuclear entry, gene/transgene expression either with or without integration. For instance, in some embodiments, a packaging cell is transformed with more than one, packaging cassette, each of which has a complementary role in the production of a viral particle.

As used herein, the term "polynucleotide" refers to all forms of DNA and RNA, whether single-stranded, double-stranded, or higher order. A polynucleotide can be chemically synthesized or can be isolated from a host cell or organism. A particular polynucleotide can contain both naturally occurring residues as well as synthetic residues.

A "retrovirus" is a virus that is composed not of DNA but of RNA. Retroviruses have an enzyme, called reverse transcriptase, which gives them the unique property of reverse transcribing their RNA into DNA after entering a cell. The retroviral DNA can then integrate into the chromosomal DNA of the host cell, to be expressed there.

A "lentivirus" is a retrovirus and can be replication-competent or replication incompetent. These viruses include, but are not limited to, human immunodeficiency viruses HIV-1 and HIV-2, simian immunodeficiency virus (SIV), feline immunodeficiency virus (FIV) and Equine Infectious Anemia virus (EIAV).

As used herein, the terms "self-inactivating" and grammatical variants thereof refer to vectors and viruses encoded thereby that when they enter a cell produce a cellular form having LTR(s) that are transcriptionally inactive in the infected cell. Generally, this is accomplished by introducing deletions or other debilitating mutations into the LTRs of the vector. As such, a "self-inactivating deletion" is a deletion in a viral vector (e.g., a lentiviral vector) that after reverse transcription lacks promoter function in the viral LTR(s). It is noted, however, that in some embodiments the self inactivating vector comprises a promoter within the body of the vector (e.g., outside the single LTR or between the two LTRs) that can remain competent to direct transcription of an operably linked nucleotide sequence.

Several terms herein can be used interchangeably. Thus, "virion," "virus," "virus particle," "viral vector," "vector particle," and "shuttle vector" can refer to a virus and a virus-based vector that are capable of introducing nucleic acids into a cell through a viral-like entry mechanism. Such vector particles can, under certain circumstances, mediate the transfer of genes into the cells they infect. Such cells are designated herein interchangeably as "host cells" or "target cells." Lentiviral vectors have been used to transfer genes by exploiting the viral infectious process. Foreign genes cloned into the lentiviral genome can be delivered to cells susceptible to infection or transduction by the lentivirus.

The term "comprising," which is synonymous with "including," "containing," or "characterized by" is inclusive or open-ended and does not exclude additional, unrecited elements or method steps. "Comprising" is a term of art used in claim language which means that the named elements are essential, but other elements can be added.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of any of the other terms.

As used herein, the term "and/or" when used in the context of a listing of entities, refers to the entities being present singly or in any combination. Thus, for example, the phrase "A, B, C, and/or D" includes A, 13, C, and D individually, but also includes any and all combinations and subcombinations of A, B, C, and D.

U.S. Patent Publication No. US-2010-0323403-A1 is incorporated herein by reference in its entirety. All references cited herein are incorporated by reference herein in their entirety.

II. Representative Embodiments

In some embodiments, the presently disclosed subject matter relates to the development of epigenetic silencing resistant integration deficient lentiviral vectors (IDLVs) and to the establishment of methodologies of target cell conditioning as an approach to enhance transgene expression from IDLVs.

A. The Development of Epigenetic-Silencing Resistant IDLVs.

A.1. Construction of IDLVs, such as HIV-1 based IDLVs, from which binding sites of host factors involved in gene silencing were deleted, such as but not limited AP-4 binding sites and/or LSF1 binding sites, and/or the majority of the U3 promoter including the NRE (as part of a SIN vector). Compensatory point mutations were introduced to retain secondary DNA structures disrupted by the aforementioned LSF1 mutations (FIGS. 3A-3D and 5A-5B). Other possible binding sites that could be deleted include AP-1 binding sites, LSF1 binding sites and YY1 binding sites.

A.2. Addition of NFkB and SP1 binding sites to the 3' U3 region of a self-inactivating IDLV, such as but not limited to HIV-1 IDLV LTR (with or without the mutations described in A.1. above) (FIGS. 3A-3D). The binding sites are binding sites for transcription activators natural (such as but not limited to ubiquitous or tissue/cell type specific) or synthetic including but not limited to binding sites for tetracycline regulated trans activators tTA, rtTA, tT65, and rtT65.

A.3. Incorporating two DNA sequences obtained from the SV40 genome (referred to herein as regions I and II) to the IDLV vector genome (either with or without the modifications described in A.1. and A.2.). The above SV40 sequences are isolated from locations upstream to the SV40 poly-adenylation signal. The sequences can be introduced either in the sense or antisense orientation (FIGS. 3A-3D and FIG. 2).

A.4. Incorporating shRNA expression cassettes into IDLVs either containing or not all or some of the modifications described in A.1-A.3 above). The shRNAs are directed to host genes involved in protein-ubiquitination and proteasome activity and epigenetic silencing, such as but not limited AP4, p300, YY1, HDACs, histone methylases, histone sumolating, histone phosphorating, proteins involved with the PRC1 or PRC2 complexes, BMI, Ring1B). To further improve the function of IDLV in gene editing applications the above methods will be combined with shRNAs directed to genes involved DNA repair pathways (such as but not limited DNA Ligase IV, Ku60, Ku70, XRCC4). shRNA expression can be controlled, for example, by PolIII promoters (such as but not limited to U6 or H1 promoters) or by various PolII promoters (FIG. 5A-5B).

B. The Establishment of Novel Methodologies of Conditioning Target Cells as an Approach to Optimize IDLVs Transduction.

B.1. shRNA expression cassettes (such as A.4. above) can be delivered into IDLV target cells at the time of, prior to and/or after IDLV transduction using a separate gene delivery system and/or the improved IDLVs hereinabove (FIGS. 5A-5B).

B.2. siRNAs directed to host factors involved in protein-ubiquitination and proteasome activity and transcriptional silencing as described in A.4. above can be introduced into IDLVs' target cells either prior to, at the time of and/or after the time of transduction.

B.3. Chemical and FDA approved drugs (which can be referred to as "small molecules"), which inhibit the host epigenetic silencing, are employed on IDLV's target cells prior to, at the time of and/or after IDLV transduction. These drugs include proteasome inhibitors, which can be employed on IDLV target cells in vitro or administered to laboratory animals and human patients in preclinical and clinical trials, respectively. The proteasome inhibitors include but are not limited to Velcade and/or MG-132, and can be administered alone or with combination with other drugs, such as but not limited HDAC inhibitors (FIGS. 6A-6B) and NHEJ inhibitors.

Figure 3:
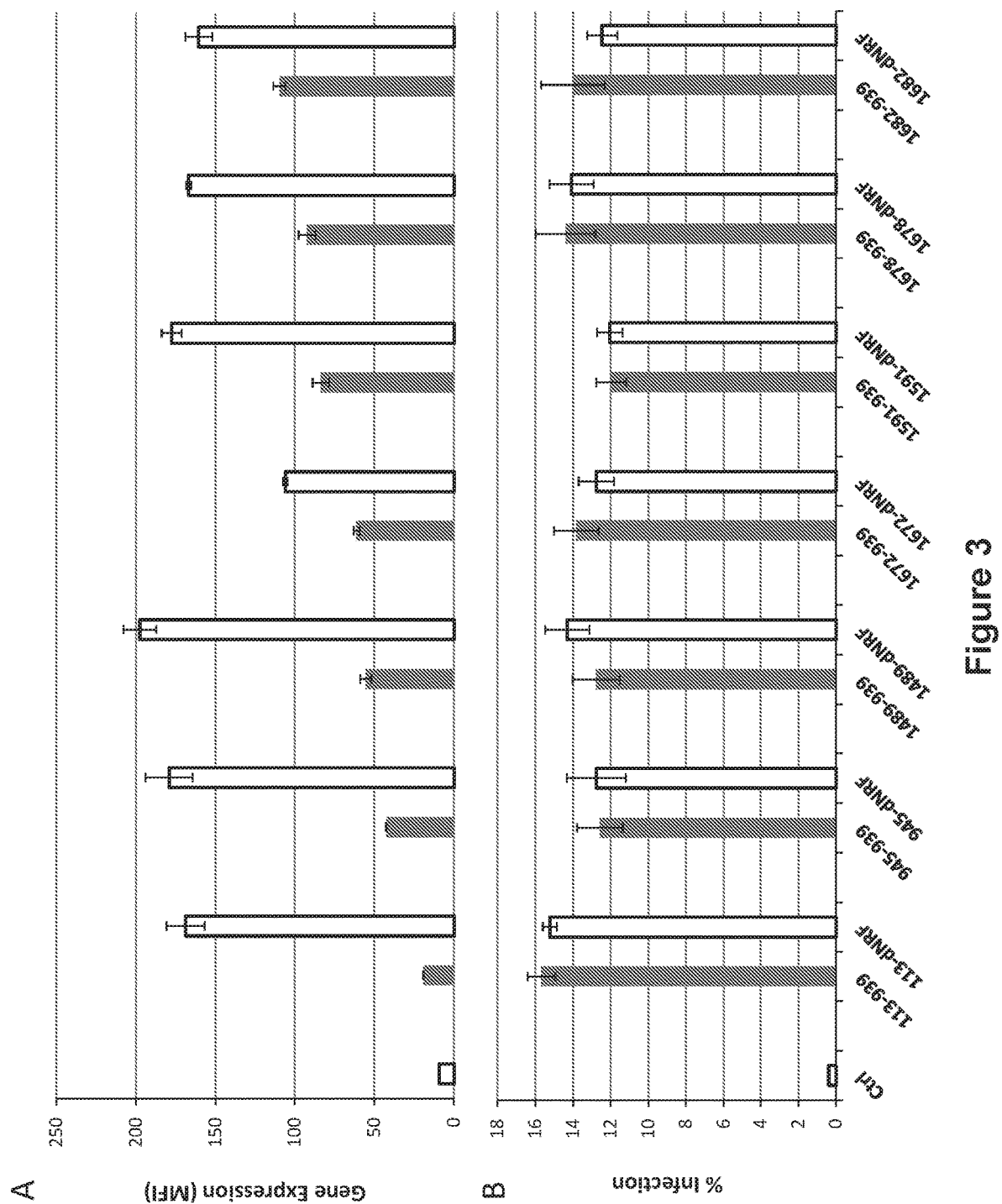
FIG. 3: Comparison of gene expression from lentiviral vectors 48 hours after infection. GFP expression from IDLVs containing various modifications (as outlined below) aimed at alleviating host transcriptional silencing following transduction of 293T cells. A) GFP expression from integration competent lentiviral vectors (ICLVs) (□) and their IDLV counterparts (■) was determined as mean fluorescence intensity (MFI) by FACscan analysis. B) Percentage of GFP positive 293T cells. C) The ratio of ICLV and IDLV GFP expression levels (of the same vector). D) Fold increase in GFP expression levels from the various IDLVs relative to the level of expression from non-integrating vTK113. Description of the modifications incorporated into the lentiviral vector below as a means to enhance IDLV transgene expression.
Figure 3:
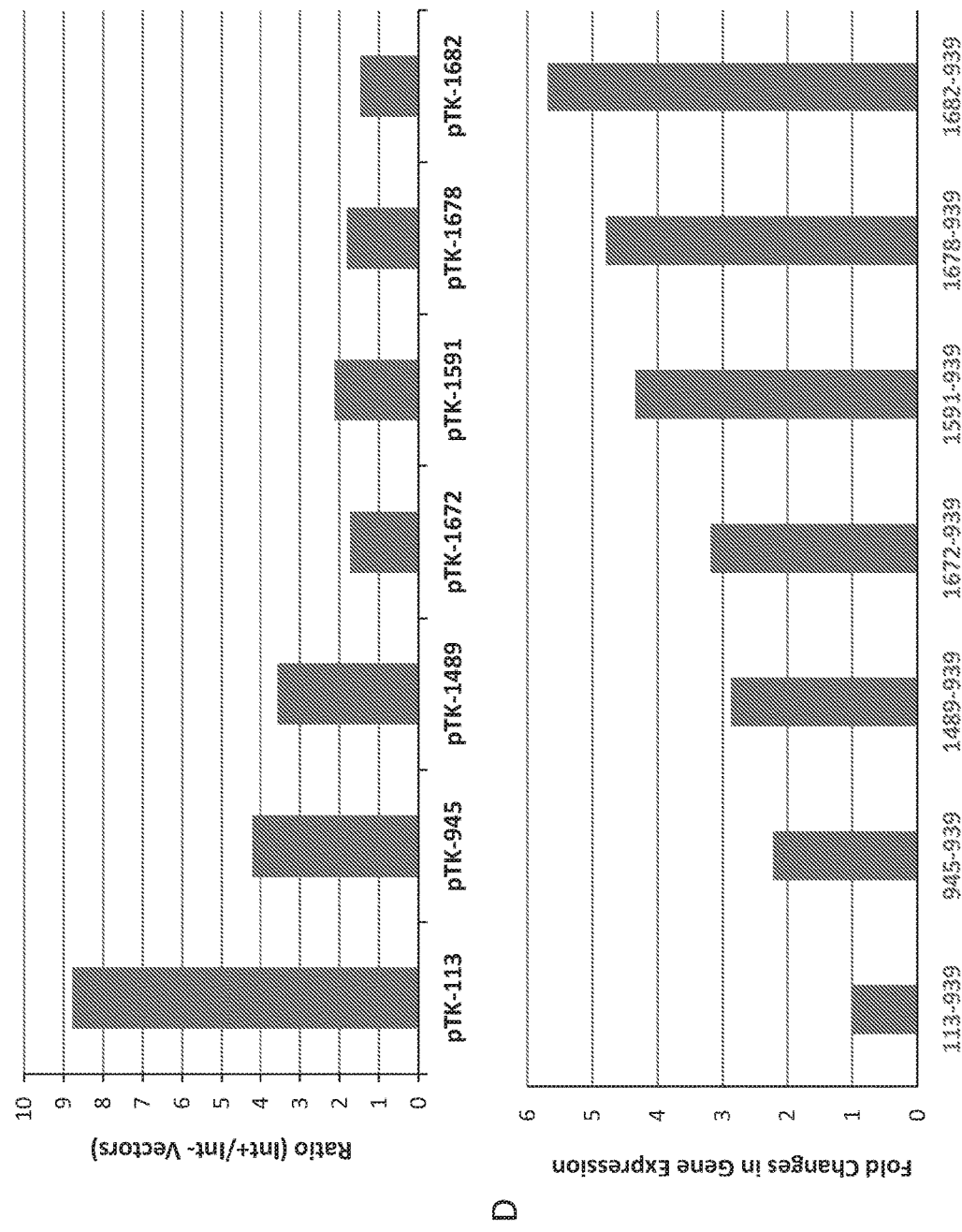

Referring now to FIGS. 3A-3D, GFP expression from IDLVs containing various modifications (as outlined below) aimed at alleviating host transcriptional silencing following transduction of 293T cells. In FIG. 3A GFP expression from integration competent lentiviral vectors (ICLVs) (gray) and their IDLV counterparts (black) was determined as mean fluorescence intensity by FACscan analysis. FIG. 3B shows percentage of GFP positive 293T cells. FIG. 3C shows the ratio ICLV and IDLV GFP expression levels (of the same vector). FIG. 3D shows fold increase in GFP expression levels from the various IDLVs relative to the level of expression from non-integrating vTK113.

Description of representative modifications incorporated into the lentiviral vectors below as an approach to enhance IDLVs' transgene expression (see also FIG. 2):

pTK113: A self-inactivating HIV-1 based vector devoid of TATA box, the NFkB-binding sites, and the SP1-binding sites.

pTK1489: A self-inactivating HIV-1 based vector devoid of the negative regulatory element, the NFkB-binding sites, and the SP1-binding sites in the U3 region. Devoid of two AP4 binding sites (one in the U3 region and the second upstream to the 3' U3. Devoid of the TATA box. Contains only part of (underlined sequence in region II right orientation as described in FIG. 2) one sequence from the SV40 poly-adenylation (pA) site region (does not contain the pA site itself).

pTK1672: A self-inactivating HIV-1 based vector devoid of the negative regulatory element site and the TATA-box in the U3 region: Devoid of two AP4 binding sites (one in the U3 region and the second upstream to the 3' U3). Contains two sequences from the SV40 poly-adenylation (pA) site region (in the right orientation as described in FIG. 2)(does not contain the pA site itself).

pTK1591: A self-inactivating HIV-1 based vector devoid of the negative regulatory element, the NFkB-binding site, and the SP1-binding site in the U3 region. Devoid of two AP4 binding sites (one in the U3 region and the second upstream to the 3' U3. Devoid of the TATA box. Contains part of (underlined sequence in region II right orientation as described in FIG. 2) one sequence from the SV40 poly-adenylation (pA) site region (does not contain the pA site itself). Devoid of LSF1 sites.

pTK1678: A self-inactivating HIV-1 based vector devoid of the negative regulatory element, the NFkB-binding site, and the SP1-binding site in the U3 region. Devoid of two AP4 binding sites (one in the U3 region and the second upstream to the 3' U3). Contains one sequence from the SV40 poly-adenylation (pA) site region (does not contain the pA site itself). Devoid of LSF1 sites. Including the 1SF1 in the parental SD.

pTK1682: A self-inactivating HIV-1 based vector devoid of the negative regulatory element and the TATA box in the U3 region. Devoid of two AP4 binding sites (one in the U3 region and the second upstream to the 3' U3. Contains two sequences from the SV40 poly-adenylation (pA) site region in the right orientation (does not contain the pA site itself). Devoid of LSF1 sites. Including the LSF1 in the parental SD.

pTK1715: A self-inactivating HIV-1 based vector devoid of the negative regulatory element and the TATA box in the U3 region. Devoid of two AP4 binding sites (one in the U3 region and the second upstream to the 3' U3). Contains two sequences from the SV40 poly-adenylation (pA) site region in the OPPOSITE orientation (does not contain the pA site itself). Devoid of LSF1 sites. Including the LSF1 in the parental SD, as described in FIG. 2, and including regions I and II in the opposite orientation.

Referring now to FIGS. 5A-5B, enhancing of IDLV expression with HDAC-directed shRNAs is shown. FIG. 5A shows a FACscan analysis of MEF re-transduced with GFP-expressing IDLV (pTK945) two days after transduction with pLKO1 vectors carrying HDAC-1 directed shRNAs. As shown, IDLV expression was enhanced by an earlier transduction with shRNA clones 3 and 4 as compared to MEF cells either not transduced with a pLKO1 vector or transduced with a pLKO1 vector expressing a control irrelevant shRNA. FIG. 5B shows incorporation of HDAC-1-directed shRNA expression cassettes into IDLVs (pTK1511, pTK1513) enhanced luciferase expression. Note that luciferase expression was normalized by vector copy number. No enhancement of IDLV expression was observed from an IDLV carrying the control GFP-directed shRNA (pTK1515).

FIGS. 6A and 6B show vector expression following Sodium Butyrate and Velcade treatment at 60 hours post infection (15 hours of drug treatment). Proteasome and HDAC inhibitors (Velcade and sodium butyrate, respectively) enhance IDLV transduction of 293T. FIG. 3A shows levels of GFP expression in 293T cells transduced with IDLVs (vTK945 or vTK1862) either in the presence or absence of the Velcade (25 mM or 50 mM) and sodium butyrate (1 mM or 2.5 mM), was determined by FACscan analysis. FIG. 3B shows the effect of the above treatments on the percentage of GFP expressing cells.

FIGS. 2A and 2B show the structure and sequence of regions I and II. The structure and sequence of region I (bold black lower case letters) and region II (grey lower case letters) either in the right orientation (pTK1672, pTK1682) or in the opposite orientation (pTK1715) is shown in FIGS. 2A and 2B, respectively.

An isolated nucleic acid is provided herein, optionally comprising a heterologous nucleotide sequence, one or two retroviral long terminal repeats (LTRs), primer binding site (PBS), a packaging signal, a rev responsive element, and a eukaryotic promoter, and either with or without a 3' polypurine tract (PPT) wherein the nucleic acid comprises one or more of the following:
  (a) a mutation, deletion or other modification of one or more binding sites for a host factor involved in gene silencing;
  (b) addition of a binding site for a transcription activator such as but not limited to NFkB binding site and/or SP1 binding site to a 3' U3 region of the vector;
  (c) one or more nucleic acid sequences from a SV40 genome, wherein the one or more sequences are obtained from a region of the SV40 genome upstream to the SV40 poly-adenylation signal (see for example regions I and II in FIG. 2);
  (d) a shRNA expression cassette, which encodes a shRNA directed to a host gene involved in epigenetic silencing and/or to a host gene involved in DNA repair and/or a host gene involve in proteasome function and their combinations; and
  (e) any combination of (a), (b), (c) and (d).

In some embodiments, vectors are provided comprising the nucleic acids. In some embodiments, recombinant viral particles are provided comprising the vectors.

In some embodiments, inducible viral vector packaging cell lines are provided comprising the vectors and at least one construct coding for proteins required for the viral vector to be packaged.

In some embodiments, methods are provided for producing integration-defective vector particles, comprising transfecting a packaging cell line with either an integration-defective lentiviral vector transfer cassette (lacking either or both the att sites and the 3' PPT) or an integration competent lentiviral vector according to the presently disclosed subject matter, wherein the packaging cell line provides an envelope protein and proteins (including integrase either integration defective mutant or integration competent), for the retroviral vector to be packaged.

In some embodiments, retroviral vector kits are provided comprising an integration-defective lentiviral vector transfer cassette (lacking either or both the att sites and the 3' PPT) according to the presently disclosed subject matter; and a packaging cell line comprising an envelope expression cassette and at least one construct coding for proteins (including integrase, either integration defective mutant or integration competent), required for the lentiviral vector to be packaged.

In some embodiments, the IDLVs of this invention can be generated by transfecting an integration competent vector cassette that contains the ATT sites into packaging cells that express a packaging cassette in which the integrase is mutated or by transfecting an integration defective vector transfer cassette into packaging cells that express either integration-defective or integration competent-integrase. Also the packaging cells should express the envelope protein.

In some embodiments, methods are provided for producing integration-defective vector particles, comprising transfecting a cell line with an integration-defective lentiviral or an integration-competent vector transfer cassette along with a packaging cassette encoding integration-defective integrase and an envelope expression cassette.

In some embodiments, methods are provided for achieving gene expression of a nucleotide sequence of interest in the cells of an animal substantially without integration of the nucleotide sequence into the animal genome, comprising infecting the cells with an integration-defective lentiviral particle of the presently disclosed subject matter that comprises the nucleotide sequence of interest. In some embodiments, the integration-defective lentiviral vectors of the presently disclosed subject matter that comprise either a viral origin of replication or a sequence that can mediate replication of the vector nucleic acid by the host cells can be maintained in dividing target cells. Conversely, in applications where only transient gene expression is desired, the integration-defective lentiviral vector transfer cassettes of the presently disclosed subject matter that do not comprise an origin of replication are useful as they are not maintained in dividing cells. For example, in some embodiments, the integration-defective lentiviral vectors of the presently disclosed subject matter lacking an origin of replication are useful for obtaining transient expression of a gene of interest in stem cells. In some embodiments, the gene of interest is a gene that directs differentiation of the stem cells. In some embodiment, the stem cells are useful for gene therapy.

In some embodiments, the sequence that can directly or indirectly mediate replication of the vector nucleic acid by the host cell includes but is not limited to a sequence recognized by the host-cell replication machinery; a sequence encoding a protein that can associate with and/or modulate host-cell replication machinery; and a sequence encoding a protein that can associate with the protein that can associate with and/or modulate host-cell replication machinery.

In some embodiments, methods are provided for achieving gene expression of a nucleotide sequence of interest in the cells of an animal by targeting integration of the nucleotide sequence into the animal genome. In some embodiments, the integration-defective vector compositions of the presently disclosed subject matter are useful as they can be more efficient than currently used non-integrating lentiviral systems. For example, the non-integrating lentiviral vector compositions and methods of the presently disclosed subject matter can be used to obtain targeted integration of a gene of interest into the genome of a host by combining the non-integrating lentiviral vector compositions and methods of the presently disclosed subject matter with known autonomous replication systems and site directed recombination systems.

In some embodiments of the presently disclosed subject matter, integration-defective lentiviral vectors are provided that comprise a heterologous sequence. In some embodiments, the heterologous sequence includes but is not limited to one or more marker genes, therapeutic genes, antiviral genes, antitumor genes, cytokine genes, genes encoding antigens, sequences that can associate with the host chromatin, sequences that encode a protein that can associate with the host DNA and the host chromatin and the nucleic acid of the vector, sequences that encode a protein having DNA methylation activity, DNA demethylation activity, cytosine deaminase activity, and combinations thereof. In some embodiments, the heterologous sequence can be employed to transiently express potentially cellular- and geno-toxic proteins whose biological functions are required for a short time. These include but are not limited to: genome-editing proteins (CAS9, Zinc-finger-nucleases, TALENs) and de-differentiation factors to generate iPS. In some embodiments, a sequence that can associate with the host chromatin is selected from the group consisting of a matrix-associated region (MAR) and a scaffold/matrix-attachment region (S/MAR). In some embodiments, the marker genes include but are not limited to β-galactosidase gene, hygromycin gene, blastocidin gene, MGMT gene, neomycin gene, puromycin gene, cytosine deaminase gene, secreted alkaline phosphatase gene, fluorescent protein genes, and combinations thereof.

In some embodiments, vectors are provided comprising the nucleic acids of the presently disclosed subject matter. In some embodiments, the vectors comprise only a single LTR. In some embodiments, the vector comprises a sequence that encodes a cis element that provides for cross-packaging of the vector in a viral particle. In some embodiments, the vectors comprise a non-functional 3' PPT or are devoid of the 3' PPT.

In some embodiments, the presently disclosed subject matter provides methods for inserting a nucleotide sequence of interest into a host genome in a site-specific manner, comprising transducing a compatible host cell with the integration-defective vectors disclosed herein, comprising in operable combination the nucleotide sequence of interest and one or more site-directed recombination sequences; and transfecting or transducing the host cell with a nucleic acid comprising a sequence encoding a nuclease or recombinase that can mediate site-specific integration at the recombination sequence.

In some embodiments, there is no second transfection/transduction step and the transfection/transduction occurs all in the same step. In some embodiments, there is no second transfection/transduction step and the nucleic acid comprising a sequence encoding a nuclease or recombinase is the integration-defective vector. In some embodiments, the gene to be inserted can be located in the U3 region of the 3' LTR sequence. In some embodiments, the vector includes one or more reporter genes.

In some embodiments, the presently disclosed subject matter provides methods for inserting a nucleotide sequence of interest into a host cell genome in a non-specific manner, comprising: transducing a host cell with an integration-defective vector of the presently disclosed subject matter comprising in operable combination the nucleotide sequence of interest and one or more transposon sequences; and transfecting or transducing the compatible host cell with a nucleic acid comprising a sequence encoding a transposase that can mediate integration into the host genome. In some embodiments, there is no second transfection/transduction step and the transfection/transduction occurs all in the same step. In some embodiments, the transfection/transduction step occurs all in the same step and the nucleic acid comprising a sequence encoding a transposase is the integration-defective vector.

In some embodiments, the transfection/transduction step occurs all in the same step and the nucleic acid comprising a sequence encoding a transposase is on a separate vector or plasmid or nucleic acid molecule than the integration-defective vector.

The presently described subject matter describes the development of non-integrating lentiviral vector compositions and methods. The non-integrating retroviral vector compositions and methods of the presently disclosed subject matter have numerous uses and benefits for achieving gene expression of nucleotide sequences of interest in animal cells.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An integration-defective lentiviral vector (IDLV) based on a parental lentivirus, the integration-defective lentiviral vector comprising one or more of the following:
    a) a mutation, deletion or other modification selected from the group consisting of
        i) deletion of an AP-4 binding site;
        ii) mutation of contiguous nucleotides CNRG to DNRG or CNYG or CNRH, wherein N=A or C or G or T, R=A or G, Y=C or T, H=A or C or T, and D=A or G or T;
        iii) deletion of a negative regulatory element (NRE);
        iv) insertion of an NFκB binding site;
        v) insertion of an SP1 binding site; and
        vi) any combination thereof;
    b) insertion of one or more binding sites for a transcription activator, which can be natural or synthetic, and incorporated into the 3' U3 region in either a self-inactivating (SIN) or a non-SIN form of the lentiviral vector and wherein the transcription activator is selected from the group consisting of SP1; NFkB; a binding site for tetracycline regulated trans activators tTA, rtTA, tT65 and/or rtT65; and any combination thereof;
    c) insertion of one or more nucleic acid sequences from a SV40 genome, wherein the one or more nucleic acid sequences are a 3f46 region, s2f2R region and/or a USE region of the SV40 genome upstream to the SV40 poly-adenylation signal, and inserted in the lentiviral vector in the 3' LTR either in the opposite or same orientation to the long terminal repeats (LTRs); and
    d) any combination of (a), (b) and (c), wherein as compared to the parental lentivirus, the integration-defective lentiviral vector resists gene silencing.

2. The lentiviral vector of claim 1, further comprising a short hairpin RNA (shRNA) expression cassette, which encodes a shRNA directed to a host gene involved in epigenetic silencing and/or ubiquitination or proteasome activity.

3. The lentiviral vector of claim 2, wherein the shRNA expression cassette is directed to a host gene involved in epigenetic silencing selected from the group consisting of AP4, p300, YY1, histone deacetylases (HDACs), histone methylases, histone ubiquitinating enzymes, histone sumoylating proteins, histone phosphorylating proteins, BMI, and Ring1B.

4. The lentiviral vector of claim 2, wherein the shRNA expression cassette is controlled by a PolIII promoter, a U6 promoter, a H1 promoter, or a PolII promoter.

5. The lentiviral vector of claim 1, further comprising a heterologous sequence.

6. The lentiviral vector of claim 5, wherein the heterologous sequence is selected from the group consisting of one or more marker genes, therapeutic genes, antiviral genes, antitumor genes, cytokine genes, genes encoding antigens, sequences that can associate with the host chromatin, sequences that encode a protein that can associate with the host DNA and with the host chromatin and with the nucleic acid of the vector; sequences that encode a protein having DNA methylation activity; sequences that encode genome-editing proteins CAS9, Zinc-finger-nucleases, or TALENs and de-differentiation factors to generate iPS; sequences that encode guide RNAs for CAS9 editing activity; sequences for homologous recombination and NHEJ-based gene editing using gene editing proteins CAS9, Zinc-finger-nucleases, or TALENs, or for gene editing following chemical and/or physical and/or biological induction of DNA damage; and any combination thereof.

7. An integration-defective lentiviral vector (IDLV) based on a parental lentivirus, the integration-defective lentiviral vector comprising one or more of the following:
   a) a mutation, deletion or other modification selected from the group consisting of
      i) deletion of an AP-4 binding site;
      ii) mutation of contiguous nucleotides CNRG to DNRG, CNYG or CNRH, wherein N=A or C or G or T, R=A or G, Y=C or T, H=A or C or T, and D=A or G or T;
      iii) deletion of a TATA box;
      iv) deletion of a negative regulatory element (NRE);
      v) insertion of an NEκB binding site;
      vi) insertion of an SP1 binding site; and
      vii) any combination thereof;
   (b) insertion of one or more binding sites for a transcription activator, which can be natural or synthetic, and incorporated into the 3' U3 region in either a self-inactivating (SIN) or a non-SIN form of the lentiviral vector and wherein the transcription activator is selected from the group consisting of SP1; NFkB; a binding site for tetracycline regulated trans activators tTA, rtTA, tT65 and/or rtT65; and any combination thereof;
   (c) insertion of one or more nucleic acid sequences from a SV40 genome, wherein the one or more nucleic acid sequences are a 3f46 region, s2f2R region and/or a USE region of the SV40 genome upstream to the SV40 poly-adenylation signal, and inserted in the lentiviral vector either in the opposite or same orientation to the long terminal repeats (LTRs);
   (d) a short hairpin RNA (shRNA) expression cassette, which encodes a shRNA directed to a host gene involved in epigenetic silencing and/or ubiquitination or proteasome activity; and
   (e) any combination of (a), (b), (c) and (d), wherein as compared to the parental lentivirus, the integration-defective lentiviral vector resists gene silencing, and further wherein the integration-defective lentiviral vector comprises a site-directed recombination site.

8. A recombinant retroviral particle comprising the vector of claim 1.

9. An inducible retroviral vector packaging cell line comprising the integration-defective lentiviral vector of claim 1 and at least one construct encoding one or more proteins required for the integration-defective lentiviral vector to be packaged and including an integration defective integrase or integration competent integrase.

10. A retroviral vector kit comprising:
   (a) the integration-defective lentiviral vector according to claim 1 in a transfer cassette; and
   (b) a packaging cell line comprising at least one construct encoding one or more proteins required for the viral vector to be packaged.

11. A method for expressing a nucleotide sequence of interest in a cell of an animal without integration of the nucleotide sequence into the genome of the cell of the animal, the method comprising infecting the cell of the animal with the recombinant retroviral particle of claim 8.

12. The method of claim 11, wherein the cell of the animal is contacted with a proteasome inhibitor and/or an HDAC inhibitor before, concurrent with and/or after contact with the recombinant retroviral particle.

13. The lentiviral vector of claim 7, wherein the shRNA expression cassette is directed to a host gene involved in epigenetic silencing selected from the group consisting of AP4, p300, YY1, histone deacetylases (HDACs), histone methylases, histone ubiquitinating enzymes, histone sumoylating proteins, histone phosphorylating proteins, BMI, and Ring1B.

14. The lentiviral vector of claim 7, wherein the shRNA expression cassette is controlled by a PolIII promoter, a U6 promoter, a H1 promoter, or a PolII promoter.

15. The lentiviral vector of claim 7, further comprising a heterologous sequence.

16. The lentiviral vector of claim 7, wherein the heterologous sequence is selected from the group consisting of one or more marker genes, therapeutic genes, antiviral genes, antitumor genes, cytokine genes, genes encoding antigens, sequences that can associate with the host chromatin, sequences that encode a protein that can associate with the host DNA and with the host chromatin and with the nucleic acid of the vector; sequences that encode a protein having DNA methylation activity; sequences that encode genome-editing proteins CAS9, Zinc-finger-nucleases, or TALENs and de-differentiation factors to generate iPS; sequences that encode guide RNAs for CAS9 editing activity; sequences for homologous recombination and NHEJ-based gene editing using gene editing proteins CAS9, Zinc-finger-nucleases, or TALENs, or for gene editing following chemical and/or physical and/or biological induction of DNA damage; and any combination thereof.

17. A recombinant retroviral particle comprising the vector of claim 7.

18. An inducible retroviral vector packaging cell line comprising the integration-defective lentiviral vector of claim 7 and at least one construct encoding one or more proteins required for the integration-defective lentiviral vector to be packaged and including an integration defective integrase or integration competent integrase.

19. A retroviral vector kit comprising:
   (a) the integration-defective lentiviral vector according to claim 7 in a transfer cassette; and
   (b) a packaging cell line comprising at least one construct encoding one or more proteins required for the viral vector to be packaged.

20. A method for expressing a nucleotide sequence of interest in a cell of an animal without integration of the nucleotide sequence into the genome of the cell of the animal, the method comprising infecting the cell of the animal with the recombinant retroviral particle of claim 17.

21. The method of claim 20, wherein the cell of the animal is contacted with a proteasome inhibitor and/or an HDAC inhibitor before, concurrent with and/or after contact with the recombinant retroviral particle.

* * * * *

UNITED STATES PATENT AND TRADEMARK OFFICE
CERTIFICATE OF CORRECTION

PATENT NO. : 11,078,495 B2
APPLICATION NO. : 15/768438
DATED : August 3, 2021
INVENTOR(S) : Tal Kafri Page 1 of 1

It is certified that error appears in the above-identified patent and that said Letters Patent is hereby corrected as shown below:

On the Title Page

(54) Title: Please correct "INTEGRATION DEFECTIVE" to read
-- INTEGRATION-DEFECTIVE --

In the Specification

Column 1, Line 2: Please correct "INTEGRATION DEFECTIVE" to read
-- INTEGRATION-DEFECTIVE --

Column 1, Lines 15-20: Please replace the paragraph under the STATEMENT OF GOVERNMENT INTEREST with the following:
-- This invention was made with government support under Grant Number DK058702 awarded by the National Institutes of Health. The government has certain rights in the invention. --

Column 7, Line 19: Please correct "itself." to read -- itself). --

Column 7, Line 25: Please correct "itself." to read -- itself). --

Column 8, Line 9: Please correct "and directed" to read -- and -directed --

Column 11, Line 57: Please correct "having LTR(s)" to read -- having 3' LTR(s) --

Column 14, Line 36: Please correct "1SF1" to read -- LSF1 --

Column 14, Line 40: Please correct "3' U3." to read -- 3' U3). --

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 4

<210> SEQ ID NO 1
<211> LENGTH: 4799
<212> TYPE: DNA
<213> ORGANISM: Artificial
<220> FEATURE:
<223> OTHER INFORMATION: pTK945 sequence

<400> SEQUENCE: 1
atatacgcgt tgacattgat tattgactag ttattaatag taatcaatta cggggtcatt      60
agttcatagc ccatatatgg agttccgcgt tacataactt acggtaaatg gcccgcctgg     120
ctgaccgccc aacgaccccc gcccattgac gtcaataatg acgtatgttc ccatagtaac     180
gccaataggg actttccatt gacgtcaatg ggtggactat ttacggtaaa ctgcccactt     240
ggcagtacat caagtgtatc atatgccaag tacgccccct attgacgtca atgacggtaa     300
atggcccgcc tggcattatg cccagtacat gaccttatgg gactttccta cttggcagta     360
catctacgta ttagtcatcg ctattaccat ggtgatgcgg ttttggcagt acatcaatgg     420
```

| | |
|---|---|
| gcgtggatag cggtttgact cacggggatt tccaagtctc caccccattg acgtcaatgg | 480 |
| gagtttgttt tggcaccaaa atcaacggga ctttccaaaa tgtcgtaaca actccgcccc | 540 |
| attgacgcaa atgggcggta ggcgtgtacg gtgggaggtc tatataagca gcgcgttttg | 600 |
| cctgtactgg gtctctctgg ttagaccaga tctgagcctg ggagctctct ggctaactag | 660 |
| ggaacccact gcttaagcct caataaagct tgccttgagt gcttcaagta gtgtgtgccc | 720 |
| gtctgttgtg tgactctggt aactagagat ccctcagacc cttttagtca gtgtggaaaa | 780 |
| tctctagcag tggcgcccga acagggactt gaaagcgaaa gggaaaccag aggagctctc | 840 |
| tcgacgcagg actcggcttg ctgaagcgcg cacggcaaga ggcgaggggc ggcgactggt | 900 |
| gagtacgcca aaaattttga ctagcggagg ctagaaggag agagatgggt gcgagagcgt | 960 |
| cagtattaag cgggggagaa ttagatcgcg atgggaaaaa attcggttaa ggccaggggg | 1020 |
| aaagaaaaaa tataaattaa aacatatagt atgggcaagc agggagctag aacgattcgc | 1080 |
| agttaatcct ggcctgttag aaacatcaga aggctgtaga caaatactgg gacagctaca | 1140 |
| accatccctt cagacaggat cagaagaact tagatcatta tataatacag tagcaaccct | 1200 |
| ctattgtgtg catcaaagga tagagataaa agacaccaag gaagctttag acaagataga | 1260 |
| ggaagagcaa aacaaaagta agaccaccgc acagcaagcg gccgctgatc ttcagacctg | 1320 |
| gaggaggaga tatgagggac aattggagaa gtgaattata taaatataaa gtagtaaaaa | 1380 |
| ttgaaccatt aggagtagca cccaccaagg caaagagaag agtggtgcag agagaaaaaa | 1440 |
| gagcagtggg aataggagct ttgttccttg ggttcttggg agcagcagga agcactatgg | 1500 |
| gcgcagcctc aatgacgctg acggtacagg ccagacaatt attgtctggt atagtgcagc | 1560 |
| agcagaacaa tttgctgagg gctattgagg cgcaacagca tctgttgcaa ctcacagtct | 1620 |
| ggggcatcaa gcagctccag gcaagaatcc tggctgtgga agataccta aaggatcaac | 1680 |
| agctcctggg gatttggggt tgctctggaa aactcatttg caccactgct gtgccttgga | 1740 |
| atgctagttg gagtaataaa tctctggaac agatctggaa tcacacgacc tggatggagt | 1800 |
| gggacagaga aattaacaat tacacaagct taatacactc cttaattgaa gaatcgcaaa | 1860 |
| accagcaaga aaagaatgaa caagaattat tggaattaga taaatgggca agtttgtgga | 1920 |
| attggtttaa cataacaaat tggctgtggt atataaaatt attcataatg atagtaggag | 1980 |
| gcttggtagg tttaagaata gttttgctg tactttctat agtgaataga gttaggcagg | 2040 |
| gatattcacc attatcgttt cagacccacc tcccaacccc gaggggaccc gacaggcccg | 2100 |
| aaggaataga agaagaaggt ggagagagag acagagacag atccattcga ttagtgaacg | 2160 |
| gatccaaaag aaaagggggg attgggggt acagtgcagg ggaaagaata gtagacataa | 2220 |
| tagcaacaga catacaaact aaagaattac aaaaacaaat tacaaaaatt caaaattttc | 2280 |
| gggagatccc ccgggctgca ggaattcgat ggaagatccc ccgggctgca ggaattcgat | 2340 |
| taatagtaat caattacggg gtcattagtt catagcccat atatggagtt ccgcgttaca | 2400 |
| taacttacgg taaatggccc gcctggctga ccgcccaacg acccccgccc attgacgtca | 2460 |
| ataatgacgt atgttcccat agtaacgcca atagggactt tccattgacg tcaatgggtg | 2520 |
| gagtatttac ggtaaactgc ccacttggca gtacatcaag tgtatcatat gccaagtacg | 2580 |
| ccccctattg acgtcaatga cggtaaatgg cccgcctggc attatgccca gtacatgacc | 2640 |
| ttatgggact ttcctacttg gcagtacatc tacgtattag tcatcgctat taccatggtg | 2700 |
| atgcggtttt ggcagtacat caatgggcgt ggatagcggt ttgactcacg ggatttcca | 2760 |

| | |
|---|---|
| agtctccacc ccattgacgt caatgggagt ttgttttggc accaaaatca acgggacttt | 2820 |
| ccaaaatgtc gtaacaactc cgccccattg acgcaaatgg gcggtaggcg tgtacggtgg | 2880 |
| gaggtctata taagcagagc tggtttagtg aaccgtcaga tccgctagcg ctaccggtcg | 2940 |
| ccaccatggt gagcaagggc gaggagctgt tcaccgggt ggtgcccatc ctggtcgagc | 3000 |
| tggacggcga cgtaaacggc cacaagttca gcgtgtccgg cgagggcgag ggcgatgcca | 3060 |
| cctacggcaa gctgaccctg aagttcatct gcaccaccgg caagctgccc gtgccctggc | 3120 |
| ccaccctcgt gaccaccctg acctacggcg tgcagtgctt cagccgctac cccgaccaca | 3180 |
| tgaagcagca cgacttcttc aagtccgcca tgcccgaagg ctacgtccag gagcgcacca | 3240 |
| tcttcttcaa ggacgacggc aactacaaga cccgcgccga ggtgaagttc gagggcgaca | 3300 |
| ccctggtgaa ccgcatcgag ctgaagggca tcgacttcaa ggaggacggc aacatcctgg | 3360 |
| ggcacaagct ggagtacaac tacaacagcc acaacgtcta tatcatggcc gacaagcaga | 3420 |
| agaacggcat caaggtgaac ttcaagatcc gccacaacat cgaggacggc agcgtgcagc | 3480 |
| tcgccgacca ctaccagcag aacaccccca tcggcgacgg ccccgtgctg ctgcccgaca | 3540 |
| accactacct gagcacccag tccgccctga gcaaagaccc caacgagaag cgcgatcaca | 3600 |
| tggtcctgct ggagttcgtg accgccgccg ggatcactct cggcatggac gagctgtaca | 3660 |
| agtccggact cagatcctac tagtaggatc tcgagggatc aagcttatcg ataatcaacc | 3720 |
| tctggattac aaaatttgtg aaagattgac tggtattctt aactatgttg ctccttttac | 3780 |
| gctatgtgga tacgctgctt taatgccttt gtatcatgct attgcttccc gtatggcttt | 3840 |
| cattttctcc tccttgtata atcctggtt gctgtctctt tatgaggagt tgtggcccgt | 3900 |
| tgtcaggcaa cgtggcgtgg tgtgcactgt gtttgctgac gcaaccccca ctggttgggg | 3960 |
| cattgccacc acctgtcagc tcctttccgg gactttcgct ttcccctcc ctattgccac | 4020 |
| ggcggaactc atcgccgcct gccttgcccg ctgctggaca ggggctcggc tgttgggcac | 4080 |
| tgacaattcc gtggtgttgt cggggaagct gacgtccttt ccatggctgc tcgcctgtgt | 4140 |
| tgccacctgg attctgcgcg gacgtccttc tgctacgtc ccttcggccc tcaatccagc | 4200 |
| ggaccttcct tcccgcggcc tgctgccggc tctgcggcct cttccgcgtc ttcgccttcg | 4260 |
| ccctcagacg agtcggatct ccctttgggc cgcctccccg catcgatacc gtcgagacct | 4320 |
| ggaaaaacat ggagcaatca caagtagcaa cacagcagct accatgctg cttgtgcctg | 4380 |
| gctagaagca caagaggagg aggaggtggg ttttccagtc acacctcagg tacctttaag | 4440 |
| accaatgact tacaaggcag ctgtagatct tagccacttt ttaaaagaaa agggggact | 4500 |
| ggaagggcta attcactccc aacgaagaca agatatccac tgaccgcacg cctgcaggct | 4560 |
| agccctcaga tcctgcatat aagcagctgc tttttgcctg tactgggtct ctctggttag | 4620 |
| accagatctg agcctgggag ctctctggct aactagggaa cccactgctt aagcctcaat | 4680 |
| aaagcttgcc ttgagtgctt caagtagtgt gtgcccgtct gttgtgtgac tctggtaact | 4740 |
| agagatccct cagacccttt tagtcagtgt ggaaaatctc tagcagggcc cgtttaaac | 4799 |

<210> SEQ ID NO 2
<211> LENGTH: 4936
<212> TYPE: DNA
<213> ORGANISM: Artificial
<220> FEATURE:
<223> OTHER INFORMATION: pTK1759 sequence

<400> SEQUENCE: 2

| | |
|---|---|
| atatacgcgt tgacattgat tattgactag ttattaatag taatcaatta cggggtcatt | 60 |

```
agttcatagc ccatatatgg agttccgcgt tacataactt acggtaaatg gcccgcctgg    120
ctgaccgccc aacgaccccc gcccattgac gtcaataatg acgtatgttc ccatagtaac    180
gccaataggg actttccatt gacgtcaatg ggtggactat ttacggtaaa ctgcccactt    240
ggcagtacat caagtgtatc atatgccaag tacgccccct attgacgtca atgacggtaa    300
atggcccgcc tggcattatg cccagtacat gaccttatgg gactttccta cttggcagta    360
catctacgta ttagtcatcg ctattaccat ggtgatgcgg ttttggcagt acatcaatgg    420
gcgtggatag cggtttgact cacggggatt tccaagtctc cacccaattg acgtcaatgg    480
gagtttgttt tggcaccaaa atcaacggga ctttccaaaa tgtcgtaaca actccgcccc    540
attgacgcaa atgggcggta ggcgtgtacg gtgggaggtc tatataagca gcgcgttttg    600
cctgtactgg gtctctctgg ttagaccaga tctgagcctg ggagctctct ggctaactag    660
ggaacccact gcttaagcct caataaagct tgccttgagt gcttcaagta gtgtgtgccc    720
gtctgttgtg tgactgcggt aactagagat ccctcagacc ctttttagtca gtgtggaaaa    780 tctctagcag tggcgcccga acagggactt gaaagcgaaa gggaaaccgc aggagctctc    840
tcgacgcagg actcggcttg ctgaagcgcg cacggcaaga ggcgagggc ggcgagaggt    900 gtctacgcca aaattttga ctagcggagg ctagaaggag agagatgggt gcgagagcgt    960
cagtattaag cggggagaa ttagatcgcg atgggaaaaa attcggttaa ggccgcgggg    1020
aaagaaaaaa tataaattaa aacatatagt atgggcaagc agggagctag aacgattcgc    1080
agttaatcgc ggcctgttag aaacatcaga aggctgtaga caaatagcgg gacagctaca    1140
accatccctt cagacaggat cagaagaact tagatcatta taatacag tagcaaccct    1200 ctattgtgtg catcaaagga tagagataaa agacaccaag gaagctttag acaagataga    1260
ggaagagcaa aacaaaagta agaccaccgc acagcaatga tcagcggccg ctgatcttca    1320
gacgcggagg aggagatatg agggacaatt ggagaagtga attatataaa tataaagtag    1380
taaaaattga accattagga gtagcaccca ccaaggcaaa gagaagagtg gtgcagagag    1440
aaaaaagagc agtgggaata ggagctttgt tccttgggtt cttggagca gcgcgaagca    1500 ctatgggcgc agcctcaatg acgctgacgg tacaggccgc acaattattg tgcggtatag    1560
tgcagcagca gaacaatttg ctgagggcta ttgaggcgca acagcatctg ttgcaactca    1620
cagtgcgggg catcaagcag ctccgcgcaa gaatcgcggc tgtggaaaga tacctaaagg    1680
atcaacagct cgcggggatt tggggttgct gcggaaaact catttgcacc actgctgtgc    1740
cttggaatgc tagttggagt aataaatctg cggaacagat gcggaatcac acgacgcgga    1800
tggagtggga cagagaaatt aacaattaca caagcttaat acactcctta attgaagaat    1860
cgcaaaaccg ccaagaaaag aatgaacaag aattattgga attagataaa tgggcaagtt    1920
tgtggaattg gtttaacata acaaattggc tgtggtatat aaaattattc ataatgatag    1980
taggaggctt ggtaggttta agaatagttt ttgctgtact ttctatagtg aatagagtta    2040
ggcagggata ttcaccatta tcgtttcaga cccacctccc aaccccgagg ggacccgaca    2100
ggcccgaagg aatagaagaa gaaggtggag agagagacag agacagatcc attcgattag    2160
tgaacggatc cattttaaaa gaaagggggg gattggggg tacagtgcag ggaaagaat    2220 agtagacata atagcaacag acatacaaac taaagaatta caaaaacaaa ttacaaaaat    2280
tcaaaatttt cgggttaacg aattcgatta atagtaatca attacggggt cattagttca    2340
tagcccatat atggagttcc gcgttacata acttacggta aatggcccgc ctggctgacc    2400
```

```
gcccaacgac ccccgcccat tgacgtcaat aatgacgtat gttcccatag taacgccaat    2460
agggactttc cattgacgtc aatgggtgga gtatttacgg taaactgccc acttggcagt    2520
acatcaagtg tatcatatgc caagtacgcc ccctattgac gtcaatgacg gtaaatggcc    2580
cgcctggcat tatgcccagt acatgacctt atgggacttt cctacttggc agtacatcta    2640
cgtattagtc atcgctatta ccatggtgat gcggttttgg cagtacatca atgggcgtgg    2700
atagcggttt gactcacggg gatttccaag tctccacccc attgacgtca atgggagttt    2760
gttttggcac caaaatcaac gggactttcc aaaatgtcgt aacaactccg ccccattgac    2820
gcaaatgggc ggtaggcgtg tacggtggga ggtctatata agcagagctg tttagtgaa    2880
ccgtcagatc cgctagcgct accggtcgcc accatggtga gcaagggcga ggagctgttc    2940
accggggtgg tgcccatcct ggtcgagctg gacggcgacg taaacggcca caagttcagc    3000
gtgtccggcg agggcgaggg cgatgccacc tacggcaagc tgaccctgaa gttcatctgc    3060
accaccggca agctgcccgt gccctggccc accctcgtga ccaccctgac ctacggcgtg    3120
cagtgcttca gccgctaccc cgaccacatg aagcagcaca cttcttcaa gtccgccatg    3180
cccgaaggct acgtccagga gcgcaccatc ttcttcaagg acgacggcaa ctacaagacc    3240
cgcgccgagg tgaagttcga gggcgacacc ctggtgaacc gcatcgagct gaagggcatc    3300
gacttcaagg aggacggcaa catcctgggg cacaagctgg agtacaacta caacagccac    3360
aacgtctata tcatggccga caagcagaag aacggcatca aggtgaactt caagatccgc    3420
cacaacatcg aggacggcag cgtgcagctc gccgaccact accagcagaa cacccccatc    3480
ggcgacggcc ccgtgctgct gcccgacaac cactacctga gcacccagtc cgccctgagc    3540
aaagacccca acgagaagcg cgatcacatg gtcctgctgg agttcgtgac cgccgccggg    3600
atcactctcg gcatggacga gctgtacaag tccggactca gatcctacta gtaggatctc    3660
gagggatcaa gcttatcgat aatcaacctc tggattacaa aatttgtgaa agattgactg    3720
gtattcttaa ctatgttgct ccttttacgc tatgtggata cgctgcttta atgcctttgt    3780
atcatgctat tgcttcccgt atggctttca ttttctcctc cttgtataaa tcctggttgc    3840
tgtctcttta tgaggagttg tggcccgttg tcaggcaacg tggcgtggtg tgcactgtgt    3900
ttgctgacgc aacccccact ggttggggca ttgccaccac ctgtcagctc ctttccggga    3960
ctttcgcttt ccccctccct attgccacgc cggaactcat cgccgcctgc cttgcccgct    4020
gctggacagg ggctcggctg ttgggcactg acaattccgt ggtgttgtcg gggaagctga    4080
cgtccttttcc atggctgctc gcctgtgttg ccacctggat tctgcgcggg acgtccttct    4140
gctacgtccc ttcggccctc aatccagcgg accttccttc ccgcggcctg ctgccggctc    4200
tgcggcctct tccgcgtctt cgccttcgcc ctcagacgag tcggatctcc ctttgggccg    4260
cctccccgca tcgataccgt cgagacgcgg aaaaacatgg agcaatcaca gtagcaaca    4320
cagcagctac caatgctgct tgtgcgcggc tagaagcaca agaggaggag gaggtgggtt    4380
ttccgctcac acctcaggta cctttaagac caatgactta caaggcagcg ctagatctta    4440
gccactttt aaaagaaaag ggggactgg aagggctaat tcactcccaa cgaagacaag    4500
cccgggcata aaatgaatgc aattgttgtt gttaacttgt ttattgcagc ttgactagag    4560
tcaataatgg ttacaaataa agcaatagca tcacaaattt cacaaataaa gcattttttt    4620
cacgatatcg agcttgctac aagggacttt ccgctgggga cttccagggg aggcgtggcc    4680
tgggcgggac tggggagtgg cgagccctca gatgctgcag cagcgccttt ttgcttgtac    4740
tgggtctctc tggttagacc agatctgagc ctgggagctc tctggctaac tagggaaccc    4800
```

-continued

```
actgcttaag cctcaataaa gcttgccttg agtgcttcaa gtagtgtgtg cccgtctgtt    4860
gtgtgactct ggtaactaga gatccctcag acccttttag tcagtgtgga aaatctctag    4920
cagggcccgt ttaaac                                                    4936

<210> SEQ ID NO 3
<211> LENGTH: 115
<212> TYPE: DNA
<213> ORGANISM: Artificial
<220> FEATURE:
<223> OTHER INFORMATION: IDLV vector sequence

<400> SEQUENCE: 3
aagctgcaat aaacaagtta acaacaacaa ttgcattcat tttatggcta gataagtgaa      60
aaaaatgctt tatttgtgaa atttgtgatg ctattgcttt atttgtaacc attat          115

<210> SEQ ID NO 4
<211> LENGTH: 129
<212> TYPE: DNA
<213> ORGANISM: Artificial
<220> FEATURE:
<223> OTHER INFORMATION: IDLV vector sequence

<400> SEQUENCE: 4
cccgggcata aaatgaatgc aattgttgtt gttaacttgt ttattgcagc ttgactagag      60
tcaataatgg ttacaaataa agcaatagca tcacaaattt cacaaataaa gcatttttt     120 cacgatatc                                                            129
```